US011813019B2

(12) United States Patent
Sela et al.

(10) Patent No.: US 11,813,019 B2
(45) Date of Patent: Nov. 14, 2023

(54) CATHETER ULTRASOUND TRANSDUCER CONTAINER

(71) Applicant: HEALIUM MEDICAL LTD, Yokneam (IL)

(72) Inventors: Ran Sela, Ramat Hasharon (IL); Yuri Megel, Haifa (IL); Shimon Eckhouse, Haifa (IL)

(73) Assignee: HEALIUM MEDICAL LTD, Yokneam (IL)

( * ) Notice: Subject to any disclaimer, the term of this patent is extended or adjusted under 35 U.S.C. 154(b) by 473 days.

(21) Appl. No.: 17/260,458

(22) PCT Filed: Aug. 22, 2019

(86) PCT No.: PCT/IL2019/050941
§ 371 (c)(1),
(2) Date: Jan. 14, 2021

(87) PCT Pub. No.: WO2020/039442
PCT Pub. Date: Feb. 27, 2020

(65) Prior Publication Data
US 2021/0267673 A1 Sep. 2, 2021

Related U.S. Application Data

(60) Provisional application No. 62/720,995, filed on Aug. 22, 2018.

(51) Int. Cl.
*A61B 18/14* (2006.01)
*A61B 18/00* (2006.01)

(52) U.S. Cl.
CPC ............ *A61B 18/1492* (2013.01); *A61B 2018/00029* (2013.01); *A61B 2018/00267* (2013.01);
(Continued)

(58) Field of Classification Search
CPC ...... A61B 18/1492; A61B 2018/00029; A61B 2018/00267; A61B 2018/00375;
(Continued)

(56) References Cited

U.S. PATENT DOCUMENTS 5,716,321 A 2/1998 Kerin et al.
5,762,066 A 6/1998 Law et al.
(Continued)

FOREIGN PATENT DOCUMENTS

EP 1009303 B1 6/2009
EP 2629683 B1 10/2015
(Continued)

OTHER PUBLICATIONS

International Search Report and Written Opinion from International Application No. PCT/IB2021/055422 dated Nov. 15, 2021.
(Continued)

*Primary Examiner* — Linda C Dvorak
*Assistant Examiner* — Abigail Bock
(74) *Attorney, Agent, or Firm* — DORSEY & WHITNEY LLP

(57) ABSTRACT

A catheter US transducer container and method of manufacture thereof including a housing, one or more cooling channels oriented longitudinally along a longitudinal axis of the container, a sealing cooling channel cover, one or more PE elements positioned on a floor of the cooling channel, the cooling channel having a trapezoid cross section at any point along the PE element.

20 Claims, 13 Drawing Sheets

(52) U.S. Cl.
CPC .............. *A61B 2018/00375* (2013.01); *A61B 2018/00577* (2013.01); *A61B 2018/00702* (2013.01); *A61B 2018/00791* (2013.01); *A61B 2018/00982* (2013.01); *A61B 2018/00994* (2013.01)

(58) Field of Classification Search
CPC .......... A61B 2018/00577; A61B 2018/00702; A61B 2018/00791; A61B 2018/00982; A61B 2018/00994
See application file for complete search history.

(56) References Cited

U.S. PATENT DOCUMENTS

| | | | |
|---|---|---|---|
| 6,064,902 | A | 5/2000 | Haissaguerre et al. |
| 8,414,508 | B2 | 4/2013 | Thapliyal et al. |
| 8,585,601 | B2 | 11/2013 | Sverdlik et al. |
| 8,696,581 | B2 | 4/2014 | Sverdlik et al. |
| 9,033,885 | B2 | 5/2015 | Thapliyal et al. |
| 9,155,588 | B2 | 10/2015 | Thapliyal et al. |
| 9,566,456 | B2 | 2/2017 | Sverdlik et al. |
| 9,737,325 | B2 | 8/2017 | Thapliyal et al. |
| 9,833,641 | B2 | 12/2017 | Thapliyal et al. |
| 9,907,983 | B2 | 3/2018 | Thapliyal et al. |
| D814,502 | S | 4/2018 | Piazza et al. |
| 9,955,946 | B2 | 5/2018 | Miller et al. |
| 9,993,666 | B2 | 6/2018 | Tsoref et al. |
| 10,286,231 | B2 | 5/2019 | Pederson et al. |
| 10,349,966 | B2 | 7/2019 | Thapliyal et al. |
| 10,368,891 | B2 | 8/2019 | Thapliyal et al. |
| 10,549,128 | B2 | 2/2020 | Phillips et al. |
| 2003/0009125 | A1 | 1/2003 | Nita et al. |
| 2003/0216721 | A1 | 11/2003 | Diederich et al. |
| 2004/0176757 | A1 | 9/2004 | Sinelnikov et al. |
| 2005/0124897 | A1 | 6/2005 | Chopra |
| 2006/0084966 | A1 | 4/2006 | Maguire et al. |
| 2006/0224090 | A1 | 10/2006 | Ostrovsky et al. |
| 2007/0265609 | A1 | 11/2007 | Thapliyal et al. |
| 2008/0045842 | A1 | 2/2008 | Furnish |
| 2010/0049099 | A1 | 2/2010 | Thapliyal et al. |
| 2010/0113906 | A1 | 5/2010 | Marple et al. |
| 2010/0168570 | A1 | 7/2010 | Sliwa et al. |
| 2010/0331658 | A1 | 12/2010 | Kim et al. |
| 2011/0201973 | A1 | 8/2011 | Stephens et al. |
| 2011/0257563 | A1 | 10/2011 | Thapliyal et al. |
| 2011/0301508 | A1 | 12/2011 | Sethuraman et al. |
| 2012/0035473 | A1 | 2/2012 | Sanghvi et al. |
| 2012/0095335 | A1 | 4/2012 | Sverdlik et al. |
| 2012/0123411 | A1 | 5/2012 | Ibrahim et al. |
| 2012/0232436 | A1 | 9/2012 | Warnking |
| 2014/0046313 | A1 | 2/2014 | Pederson et al. |
| 2014/0081301 | A1 | 3/2014 | Tran et al. |
| 2014/0088630 | A1 | 3/2014 | Tran et al. |
| 2014/0163360 | A1 | 6/2014 | Stevens-wright et al. |
| 2014/0163372 | A1 | 6/2014 | Deladi et al. |
| 2014/0276759 | A1 | 9/2014 | Kim et al. |
| 2015/0011987 | A1 | 1/2015 | Kobayashi et al. |
| 2015/0105715 | A1 | 4/2015 | Pikus et al. |
| 2015/0257779 | A1 | 9/2015 | Sinelnikov et al. |
| 2016/0016016 | A1* | 1/2016 | Taylor ............ A61B 17/320068 606/169 |
| 2016/0113699 | A1 | 4/2016 | Sverdlik et al. |
| 2016/0287912 | A1 | 10/2016 | Warnking |
| 2016/0317843 | A9 | 11/2016 | Arenson et al. |
| 2017/0056057 | A1 | 3/2017 | Thapliyal et al. |
| 2017/0065339 | A1 | 3/2017 | Mickelsen |
| 2017/0354395 | A1 | 12/2017 | Lupotti et al. |
| 2017/0354461 | A1 | 12/2017 | Rothman et al. |
| 2018/0199911 | A1 | 7/2018 | Harks et al. |
| 2018/0345046 | A1 | 12/2018 | Gallup |
| 2020/0093505 | A1 | 3/2020 | Sinelnikov et al. |
| 2020/0114176 | A1 | 4/2020 | Phillips et al. |

FOREIGN PATENT DOCUMENTS

| | | |
|---|---|---|
| WO | 0182778 A2 | 11/2001 |
| WO | 2012120495 A2 | 9/2012 |
| WO | 2014022777 A1 | 2/2014 |
| WO | 2017074726 A1 | 5/2017 |
| WO | 2020039442 A1 | 2/2020 |
| WO | 2022180511 A1 | 9/2022 |

OTHER PUBLICATIONS

Invitation to Pay Additional Fees for International Application No. PCT/IB2021/055422 dated Sep. 23, 2021.
International Search Report and Written Opinion from International Application No. PCT/IL2019/050941 dated Nov. 25, 2019.
U.S. Appl. No. 62/720,995, filed Aug. 22, 2018.
Lewalter, et al., "An update and current expert opinions on percutaneous left atrial appendage occlusion for stroke prevention in atrial fibrullation", Europe Society of Cardiology, 15, 2013, pp. 652-656.
International Search Report and Written Opinion from International Application No. PCT/IB2022/051547 dated Jul. 18, 2022.
Invitation to Pay Additional Fees for International Application No. PCT/IB2022/051547 dated May 27, 2022.
U.S. Appl. No. 63/043,832, filed Jun. 25, 2020.
Extended European Search Report for European Application No. 19852790.5 dated Aug. 30, 2021.
U.S. Appl. No. 17/260,458, filed Jan. 14, 2021.
Office Action for Japanese Application No. 202134843 dated Jun. 26, 2023.

* cited by examiner

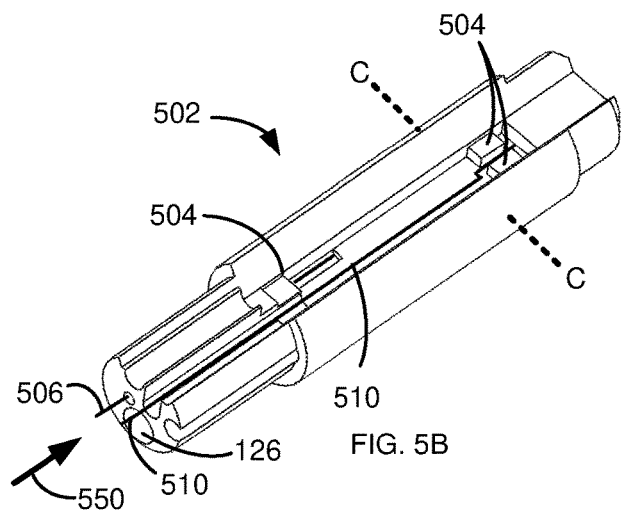
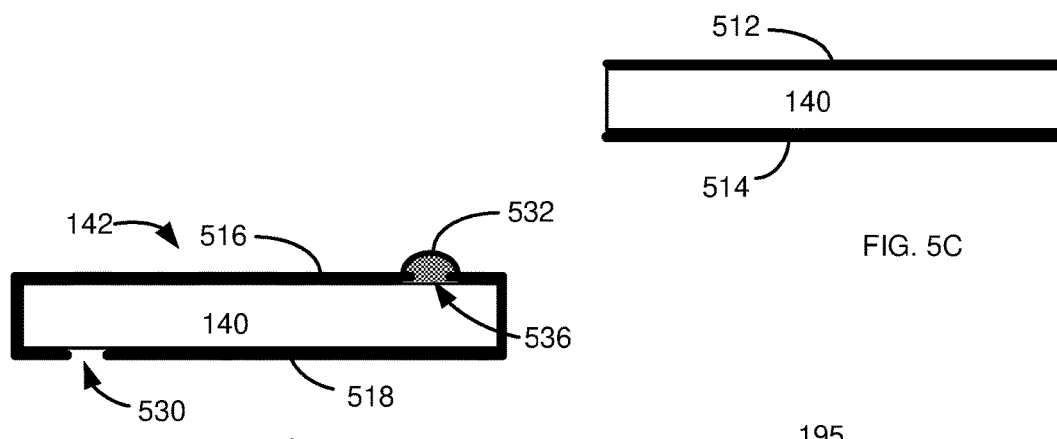
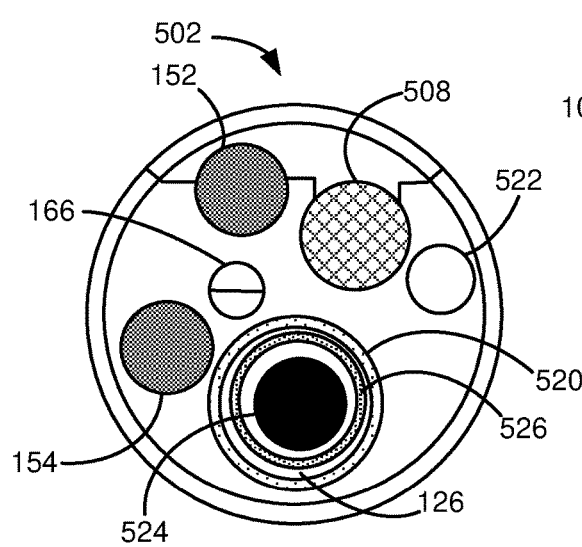
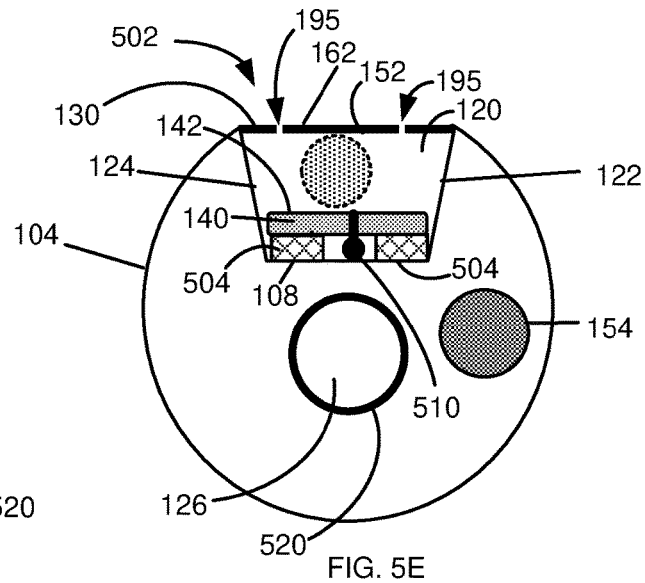

CATHETER ULTRASOUND TRANSDUCER CONTAINER

CROSS REFERENCE TO RELATED APPLICATIONS

This application is a US national phase application of PCT Application No. PCT/IL2019/050941 to Sela (published as WO 2020-039442), filed Aug. 22, 2019, which claims the benefit of priority to U.S. Provisional Patent Application No. 62/720,995, filed Aug. 22, 2018, entitled "CATHETER ULTRASOUND TRANSDUCER CONTAINER". The contents of the above application are all incorporated by reference as if fully set forth herein in its entirety.

FIELD OF THE INVENTION

The invention, in some embodiments thereof, relates to catheter ultrasound (US) transducers.

BACKGROUND

Catheter ablation is a procedure used to remove or terminate a faulty electrical pathway from sections of the heart, especially in those who are prone to developing cardiac arrhythmias and to restore the heart to its normal rhythm. Ablation procedures are commonly carried out by radiofrequency (RF) ablation and cryoablation.

Catheter ablation is a specialist catheter-based procedure that ablates abnormal heart muscle tissue. The procedure is used particularly in patients whose cardiac arrhythmia cannot be controlled with medication.

Catheter ablation involves advancing several flexible catheters into the patient's blood vessels, usually either in the femoral vein, internal jugular vein, or subclavian vein. The catheters are then advanced towards the heart. Electrical impulses are then used to induce the arrhythmia and local heating or freezing is used to ablate the abnormal tissue that is causing it. Catheter ablation is usually performed by an electrophysiologist (a specially trained cardiologist) in a catheter lab or a specialized EP lab.

The foregoing examples of the related art and limitations related therewith are intended to be illustrative and not exclusive. Other limitations of the related art will become apparent to those of skill in the art upon a reading of the specification and a study of the figures.

SUMMARY

There is provided, in accordance with some embodiments of the invention a catheter US transducer container, including a housing, one or more cooling channels, oriented longitudinally along a longitudinal axis of the container, a sealing cooling channel cover, one or more PE elements positioned on a floor of the cooling channel and having an emitting surface facing the cover, wherein the cooling channel has a trapezoid cross section at any point along the PE element.

In some embodiments, an emitting surface of at least one PE element is oriented in parallel to the cooling channel cover. In some embodiments, the floor includes the short base of the trapezoid. In some embodiments, the housing further includes at least one fluid inlet opening to a proximal end of the cooling channel and at least one fluid outlet located at a distal end of the cooling channel and/or located inside the fluid collecting and diverting chamber and a fluid collecting and diverting chamber coupled to a distal end of the cooling channel.

In some embodiments, the housing includes at least one post coupled to the floor of the cooling channel and supports the PE element, forming a gap between the floor and the PE element. In some embodiments, the PE element is angled with respect to the floor of the cooling channel. In some embodiments, the cooling channel cover and the emitting surface of the PE element are parallel. In some embodiments, the cooling channel is configured to promote laminar flow of fluid flowing between the cover and the emitting surface of the PE element.

In some embodiments, the rate of flow of the fluid flowing the cooling channel is adjusted to the viscosity of the fluid and fluid velocity within the cooling channel is maintained below a threshold at which it becomes turbulent. In some embodiments, in operation, the laminar flow promoted by the geometry and dimensions of the fluid channel. In some embodiments, the laminar flow effected by the geometry and design of the cooling channel forms a temperature gradient in the fluid in the cooling channel along a distance (L) between the emitting surface of the PE element and the fluid channel cover and the temperature gradient maintains a temperature at the cooling fluid channel cover at or below temperature of blood surrounding the container.

In some embodiments, the container includes a plurality of PE elements angled with respect to one another. In some embodiments, the container includes a plurality of PE elements at least one of which is angled with respect to the cooling channel floor. In some embodiments, at least one of the PE elements is an ablative PE element and at least one of the PE elements is an imaging PE element. In some embodiments, a depth (d) of the cross-section of the cooling channel is smaller than the radius of the housing. In some embodiments, a diameter of the container is unchangeable. In some embodiments, the housing includes at least one temperature sensor.

In some embodiments, the PE element includes a first and a second electrodes, the first electrode disposed along the emitting surface and a second electrode disposed along an opposite surface of PE element, wherein the PE element includes a first and a second electrodes, the first electrode is disposed along at least a portion of the PE element emitting surface and around one end of the PE element and a second electrode disposed along at least a portion of an opposite surface of PE element and around an opposite end of the PE element.

In some embodiments, the electrodes are isolated from each other by at least one gap on the emitting surface and the opposite surface of the PE element, wherein the at least one gap is bridged by an insulating adhesive.

In some embodiments, the catheter includes at least one positioner. In some embodiments, the positioner is in a form of a basket. In some embodiments, the positioner is in a form of a coil. In some embodiments, the positioner is in a form of an umbrella. In some embodiments, the positioner may comprise and opening facing towards the US transducer container. In some embodiments, the positioner may comprise an opening facing away from US transducer container. In some embodiments, the positioner includes at least one opening. In some embodiments, the positioner is non-occluding. In some embodiments, the positioner is disposed over the container. In some embodiments, the container is disposed between two positioners.

In some embodiments, the container is rotatable about the catheter. In some embodiments, the container includes a beam collimating acoustic lens. In some embodiments, the beam collimating acoustic lens is configured to collimate an US beam and generate a jet effect in surrounding blood along the beam pathway through the blood. In some embodiments, the collimating acoustic lens is configured to direct the jet effect towards and cool the ablated tissue.

In some embodiments, the catheter includes a medicament outlet in propinquity to the container and wherein the collimating acoustic lens is configured to direct the jet effect towards and drive the medicament into tissue.

In some embodiments, the processor is configured to adjust the level of energy emitted from the PE element based on at least one of distance measured from the emitting surface of the PE element to the tissue wall, tissue thickness, duration of energy delivery, change in amplitude and/or phase of ultrasound signal returning from the tissue and reduction of recorded electrical potential signals. In some embodiments, the processor is configured to adjust fluid flow velocity in the cooling channel based on the temperature reading and beam energy level. In some embodiments, the cooling fluid channel includes a fluid inlet and wherein the processor is configured to adjust fluid temperature at the inlet based on the temperature reading and beam energy level.

In some embodiments there is provided a method of manufacture of a catheter US transducer container, including molding a housing having at least one cooling fluid channel, at least one PE element mounting post, and at least one wiring conduit, laying electrical and data wiring inside the wiring conduits, mounting at least one PE element on the at least one mounting post and within designated cavities in cooling channel and connecting wiring, sealing a perimeter of the PE element to walls of the cooling channel attaching a cooling fluid collecting and diverting chamber to a distal end of the housing, and placing an insulating cover over the housing and cooling channel, shrinking the cover and tightly sealing the housing and the cooling channel.

The following embodiments and aspects thereof are described and illustrated in conjunction with systems, tools and methods which are meant to be exemplary and illustrative, not limiting in scope.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 5A, 5B, 5C, 5D, 5E, 5F, 5G, 5H and 5I, which are perspective view and cross section view simplified illustration of method of manufacturing a container transducer in accordance with some embodiments of the invention;

DETAILED DESCRIPTION

Figure 1A:
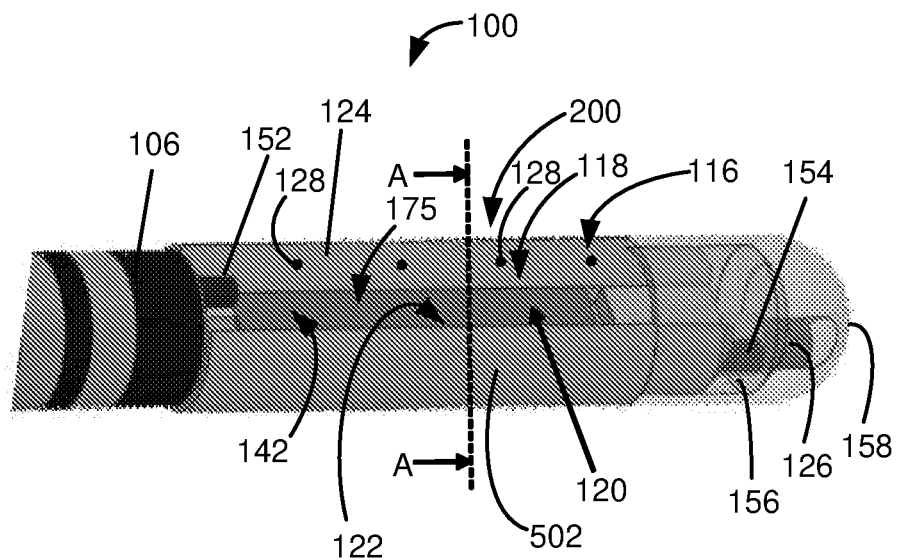
FIGS. 1A, 1B, 1C, 1D, 1E, 1F, 1G, 1H, 1I, 1J and 1K are perspective view and cross section view simplified illustration of an US transducer container, according to some embodiments of the invention.

According to an aspect of some embodiments of the invention there is provided a catheter US transducer having one or more PiezoElectric (PE) elements (ceramics) and one or more cooling systems that regulate the temperature of the transducer and/or volumes adjacent to the US transducer (e.g., cooling fluid). According to some embodiments, the US transducer and the cooling system are housed within a container. In some embodiments, the container comprises one or more apertures.

In some embodiments, the cooling systems comprises cooling fluid. In some embodiments, the cooling system is circulated within the container. In some embodiments, the container is sealed from the environment. In some embodiments, the cooling fluid does not contact fluid surrounding the catheter and/or the container. In some embodiments, the external diameter of the container is smaller than the external diameter of the catheter. In some embodiments, the external diameter of the container is the same as the external diameter of the catheter. In some embodiments, the external diameter of the container is larger than the external diameter of the catheter. In some embodiments, the temperature of the external surface of the US transducer container is maintained below 45° C. In some embodiments, the container is rigid. In some embodiments, the external diameter of the US transducer container is unchanged during operation.

According to an aspect of some embodiments of the invention there is provided an US transducer container sized and fitted to be positioned along a catheter and/or within a delivery catheter. In some embodiments, the US transducer emitting surface comprises a plane one dimension of which is oriented in parallel to a longitudinal axis of the catheter. In some embodiments, the US transducer emitting surface comprises a plane one dimension of which is angled with respect to the longitudinal axis of the catheter. In some embodiments, the US transducer comprises a plurality of emitting surfaces, in which at least one emitting surface comprises a plane one dimension of which is oriented in parallel to a longitudinal axis of the catheter and at least a second emitting surface comprises a plane having at least one dimension that is angled with respect to the longitudinal axis of the catheter. In some embodiments, the US transducer comprises a plurality of emitting surfaces, in which at least two emitting surfaces are angled with respect to the longitudinal axis of the catheter. In some embodiments, the at least two emitting surfaces are inclined towards each other with respect to the longitudinal axis of the catheter.

According to an aspect of some embodiments of the invention there is provided an US transducer container sized and fitted to be positioned along a catheter and/or within a delivery catheter. In some embodiments, the US transducer container comprises a collimating acoustic lens. In some embodiments, the US transducer emits a collimated beam. In some embodiments, the collimated beam generates one or more jets in the blood stream (a jet effect). In some embodiments, a collimated beam generates the jet effect in surrounding blood along the beam pathway through the blood. In some embodiments, the generated jets are at the same temperature as the medium in which they are generated.

According to an aspect of some embodiments of the invention there is provided one or more US transducer positioners 702s. In some embodiments, the positioner 702 is in a form of a basket. In some embodiments, the positioner 702 is in a form of a cage. In some embodiments, the positioner 702 is in a form of a coil. In some embodiments, the transducer catheter comprises two positioners 702s disposed one on either side of the US transducer container. In some embodiments, the positioner 702 is made of a shape memory alloy. In some embodiments, the positioner 702 envelops the US transducer container. In some embodiments, the positioner 702 comprises an aperture. In some embodiments, the diameter of the aperture is greater than the diameter of the US beam emitted through the aperture.

According to some embodiments of the invention, the catheter comprises one or more therapeutic agent delivery nozzles configured to deliver a therapeutic agent into a volume within an emitted US beam. In some embodiments, the US transducer emits collimated beam energy. In some embodiments, the collimated beam energy generates one or more jets in the blood stream (a jet effect) that drive the therapeutic agent via the jet stream towards the tissue surface.

General

Reference is now made to FIGS. 1A, 1B, 1C, 1D, 1E, 1F, 1G, 1H, 1I, 1J and 1K, which are perspective view and cross section view simplified illustrations of a catheter US transducer container according to some embodiments of the invention. According to some embodiments of the invention there is provided a catheter US transducer 175 housed in container 100. In some embodiments, container 100 comprises one or more cooling systems 200 that regulate the temperature of the transducer 175 by streaming cooling fluid over and around the US transducer. According to some embodiments, the US transducer 175 and the cooling system 200 are housed within the container 100. In some embodiments, the container 100 comprises one or more apertures 118. In some embodiments, one or more of the apertures 118 comprise one or more blood-contact surfaces 116.

In some embodiments, the container 100 is fluidly sealed from the environment. In some embodiments, the cooling fluid does not contact fluid surrounding the catheter and/or the container 100. In some embodiments, the external diameter of the container 100 is smaller than the external diameter of the catheter 106. In some embodiments, the external diameter of the container 100 is the same as the external diameter of the catheter. In some embodiments, the external diameter of the container 100 is larger than the external diameter of the catheter 106. In some embodiments, the temperature of the external surface of the US transducer container 100 is maintained below 45° C.

In some embodiments, US transducer container 100 is attached to a catheter 106 end and functionally coupled to one or more sources of cooling fluid, power (e.g., electric power), vacuum and unidirectional and/or bidirectional data communication conduits. Catheter 106 comprises a main lumen 126. The term "Cooling Fluid" as used herein relates to a fluid having a temperature configured to maintain a temperature of a blood-contact surface 116 no higher than the surrounding blood temperature.

In some embodiments, the US transducer 175 container 100 is mounted at a distal end of a catheter 106. In some embodiments, the US transducer container 100 is mounted proximally to the catheter tip. In some embodiments, the external diameter of the US transducer container 100 is unchanged before, during and/or post operation.

As used herein the term "Proximal" means closer to the user of the US catheter and the term "Distal" means closer to the tip of the US catheter. The term "proximally" means towards the user of the US catheter and the term "Distally" means away from the user of the US catheter and towards the tip of the US catheter.

Figure 1B:
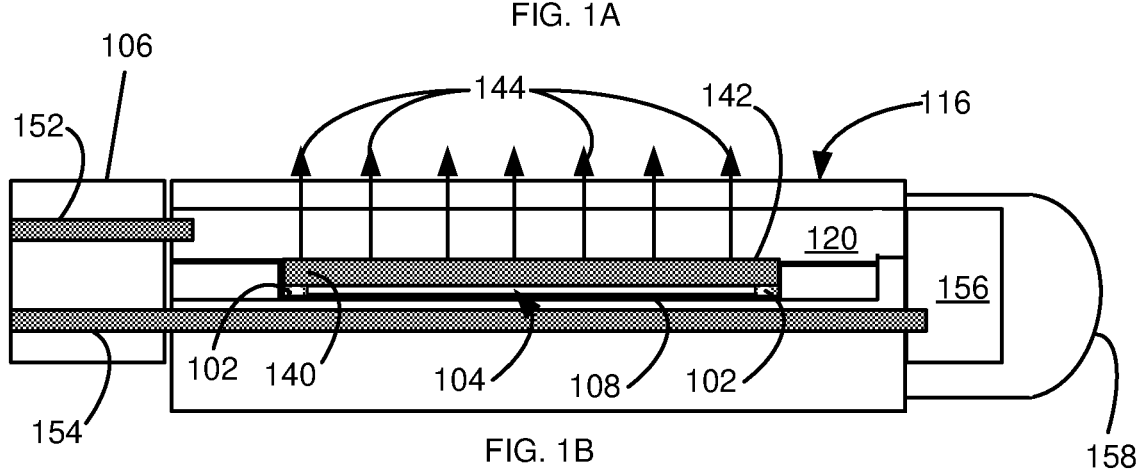

In some embodiments, and as shown in the exemplary embodiments depicted in FIGS. 1A and 1B, catheter ultrasound transducer container 100 has a cylindrical geometry and comprises a housing 502. In some embodiments, at least one or more portions of housing 502 are solid. In some embodiments, housing 502 comprises one or more hollow conduits that provide passageways for example, for electrical and/or data communication wiring, a coolant, medicament and/or any other fluid from a source to the US transducer container 100. In some embodiments, a solid portion of housing 502 fills over 50% of the cross-section of housing 502. In some embodiments, the solid portion of housing 502 fills between 50% and 75% of the cross-section of housing 502.

In some embodiments, housing 502 comprises one or more trough-form cooling channels 120, disposed longitudinally along a longitudinal axis of container 100 and catheter 106 and configured to promote laminar fluid flow. In some embodiments, cooling channel 120 comprises a trapezoid cross-section (FIG. 2A) defined by a floor 108 and walls 122/124, on lateral sides of floor 108 forming an obtuse angle between floor 108 and walls 122/124. In some embodiments, walls 122/124 are positioned parallel to the longitudinal axis of container 100 and catheter 106. In some embodiments, the trapezoid is an isosceles trapezoid. In some embodiments, floor 108 comprises the short base of the trapezoid.

In some embodiments, housing 502 comprises one or more posts 102 that protrude from floor 108 and support one or more piezoelectric (PE) elements 140 Forming a gap between PE element 140 and floor 108. The length of cooling channel 120 is at least the same as the length of PE element 140. In some embodiments, cooling channel 120 has a trapezoid cross section at any point along at least one or more PE elements 140.

In some embodiments, catheter ultrasound transducer container 100 cooling channel 120 comprises one or more cooling fluid inlets 152 disposed at a proximal and of cooling channel 120. Cooling channel 120 opens distally to a fluid (e.g., coolant) cooling fluid diverting chamber 156. In some embodiments, housing 502 comprises a cooling fluid outlet 154 disposed at a distal end of cooling channel 120 and/or inside a fluid cooling fluid diverting chamber 156. In some embodiments, fluid cooling fluid diverting chamber 156 is configured to collect fluid flowing through cooling channel 120 over an emitting surface 142 of PE element 140 and exiting from the distal end thereof, and divert the fluid to drain into fluid outlet 154 and catheter 106 to a fluid collection reservoir.

In some embodiments, catheter US transducer container 100 is fluidly sealed and isolated from the surroundings e.g., blood. In some embodiments, catheter US transducer container 100 comprises a sealing cooling channel cover 130. In some embodiments, and as explained in greater detail herein, cover 130 comprises at least two surfaces: a PE element 140-facing surface and a blood contact surface 116 facing away from PE element 140. In some embodiments, fluid (e.g., coolant) inlet 152 disposed between cover 130 and the emitting surface 142 of PE element 140. In some embodiments, cover 130 is parallel to emitting surface 142 of PE element 140. In some embodiments, fluid flowing from inlet 152 through cooling channel 120 and between two flat surfaces of PE element 140 and cover 130 flows at a laminar flow. The rate of flow of the coolant fluid is adjusted to the viscosity of the fluid and fluid velocity is maintained below a threshold at which it becomes turbulent.

In some embodiments, and optionally, cooling channel 120 comprises one or more cooling fluid side inlets 128 in walls 122/124 and fluid flowing from side inlets 128 through cooling channel 120 and between two flat surfaces of PE element 140 and cover 130 flows at a laminar flow.

In some embodiments, cooling channel 120 cover 130 completes the trapezoid cross-section. In some embodiments, cover 130 is flat. In some embodiments, cover 130 is curved. In some embodiments, the depth (d) (FIGS. 2A and 2C) of the cross-section of cooling channel 120 is smaller than the radius of housing 502. In some embodiments, the depth (d) of the cross-section of cooling channel 120 is less than two thirds of the radius of housing 502. In some embodiments, the depth (d) of the cross-section of cooling channel 120 is between two thirds and half of the radius of housing 502.

In some embodiments, cover 130 spans less than 50% of the circumference of housing 502. In some embodiments, cover 130 spans between 40% and 50% of the circumference of housing 502. In some embodiments, cover 130 spans between 30% and 40% of the circumference of housing 502. In some embodiments, cover 130 spans between 20% and 30% of the circumference of housing 502. In some embodiments, cover 130 spans less than 20% of the circumference of housing 502.

PE element 140 emitting surface 142 is positioned parallel to a floor 108 of cooling channel 120 and to container 100 longitudinal axis and emits US energy radially outwards in a direction generally perpendicular to the emitting surface 142 of PE element 140. In some embodiments, PE element 140 is mounted on posts 102 defining a gap 104 between PE element 140 and floor 108 of cooling channel 120. In some embodiments, gap 104 comprises air that forms a buffer that blocks ultrasonic energy from being emitted in the direction of channel floor 108 and increases the energy emitted radially outward.

Figure 1C:
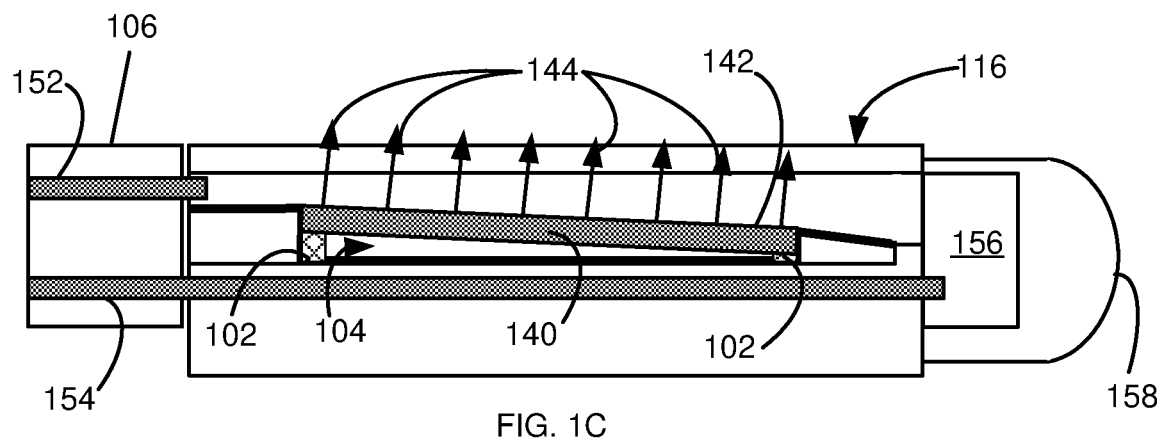
Figure 1D:
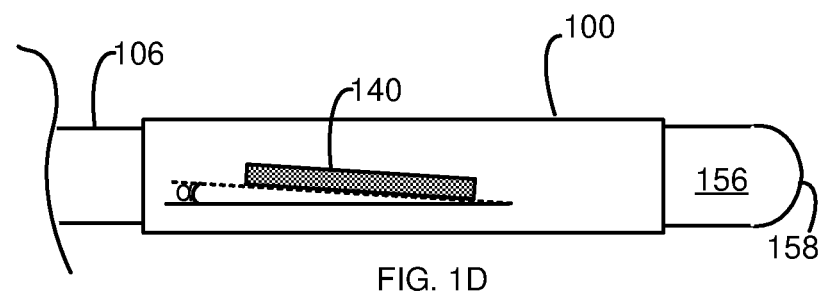

In some embodiments, and as shown in FIG. 1C, PE element 140 is inclined sloping generally forwards (distally) towards the catheter tip 158 with respect to floor 108 of cooling channel 120 and to container 100 longitudinal axis and is configured to emit US energy generally angled forward (distally) with respect to floor 108 of cooling channel 120 and container 100 longitudinal axis. In some embodiments, and as depicted in FIG. 1D an angle of inclination ($\alpha$) between 1 and 80 degrees. In some embodiments, the angle of inclination ($\alpha$) is between 20 and 70 degrees, between 30 and 60 degrees or between 40 and 50 degrees.

Figure 1E:
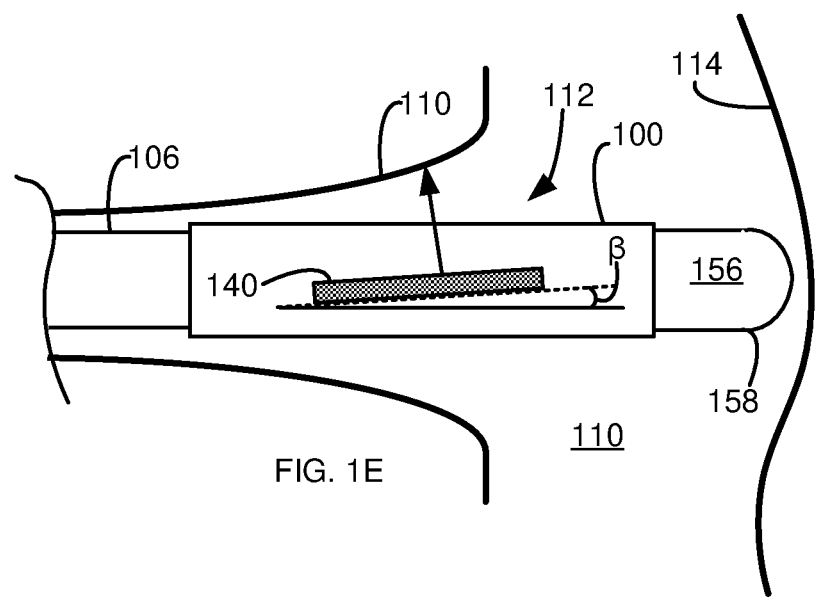

In some embodiments, and as depicted in FIG. 1E, PE element 140 is inclined sloping generally proximally (away from catheter tip 158) with respect to floor 108 of cooling channel 120 and to container 100 longitudinal axis and is configured to emit US energy generally angled backwards (proximally) with respect to floor 108 of cooling channel 120 and container 100 longitudinal axis at an angle of inclination ($\beta$) between 1 and 80 degrees. In some embodiments, the angle of inclination ($\beta$) is between 20 and 70 degrees, between 30 and 60 degrees or between 40 and 50 degrees.

A potential advantage of this configuration is in that US energy can be emitted generally perpendicularly towards inclined or sloppy anatomical tissue e.g., openings or ostia 112 of narrowing blood vessels 110 wall for ablation purposes. As demonstrated in FIG. 1F, tip 158 of catheter 106 is limited from further introduction by a wall 114 of blood vessel 110 and in some cases treatment of tissue in the ostium 112 of a blood vessel 110 can be difficult to impossible.

Figure 1F:
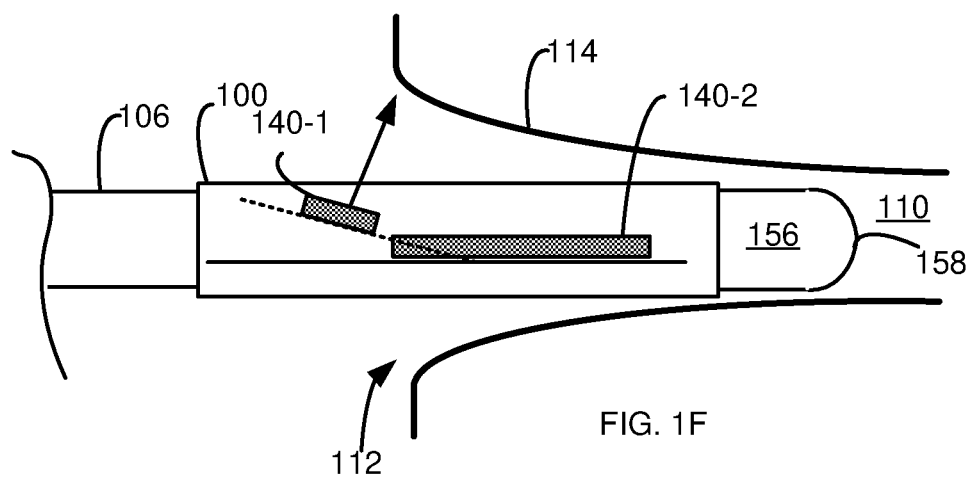

In some embodiments, and as shown in FIG. 1F, US transducer container 100 comprises one or more PE elements 140-1 inclined sloping generally forwards (distally) towards the catheter tip 158 and one or more PE elements 140-2 parallel to floor 108 of cooling channel 120 and container 100 longitudinal axis. A potential advantage of this configuration is in that US energy can be emitted generally forward towards areas having limited access, e.g., ostium 112 of narrowing blood vessel 110, for ablation purposes. In this configuration ablation US energy is emitted from PE element 140-1 from a safe distance but may still be imaged by PE element 140-2 without harm to the treated tissue.

Figure 1G:
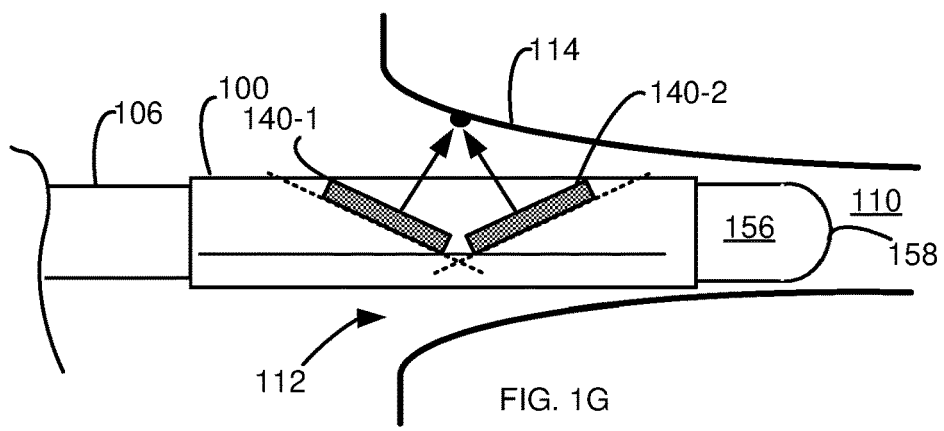

In some embodiments, and as shown in FIG. 1G, US transducer container 100 comprises one or more PE elements 140-1 inclined sloping generally forwards (distally) towards the catheter tip 158 and one or more PE elements 140-2 inclined sloping generally backwards (proximally) away from the catheter tip 158. A potential advantage of this configuration is in that ablation energy can be emitted by one of PE elements 140 (e.g., PE element 140-1) and the progress of the ablative procedure imaged by the second PE element (e.g., PE element 140-2). In this configuration ablation US energy is emitted from PE element 140-1 from a safe distance but may still be imaged by PE element 140-2 without harm to the treated tissue.

Figure 1H:
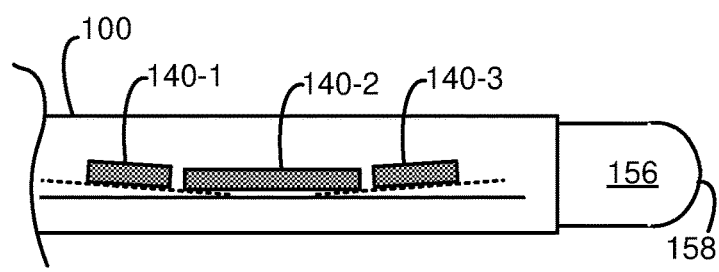
Figure 1I:
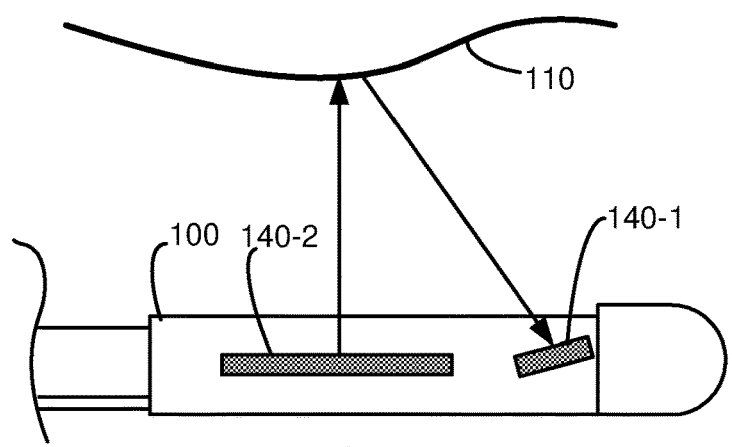

In some embodiments, and as shown in FIG. 1H, US transducer container 100 comprises one or more PE elements 140-1 inclined sloping generally forwards (distally) towards the catheter tip 158, one or more PE elements 140-2 parallel to floor 108 of cooling channel 120 and container 100 longitudinal axis and one or more PE elements 140-3 inclined sloping generally proximally (away from catheter tip 158). A potential advantage of this configuration is in that US energy can be emitted generally forward and perpendicularly towards areas having angled or steeped anatomy (e.g., ostia 112 of narrowing blood vessels 110) for ablation purposes, or generally backward towards areas having angled or steeped anatomy (e.g., ostia 112 of narrowing blood vessels 110) for ablation purposes. In this configuration ablation US energy is emitted from PE elements 140-1 and/or 140-3 from a safe distance but may still be imaged by PE element 140-2 without harm to the treated tissue.

In some embodiments, two ablating PE elements 140 (e.g., FIG. 1J, 140-1 and 140-2) are set in container 100 spaced from one another by a gap e.g., wider than 1 mm A potential advantage in this configuration is in that concurrent activation of the PE elements and concurrent full rotation of the US transducer container 100 forms two adjacent circumferential lesion rings effecting a dual lesion block.

A potential advantage of the configuration depicted in FIGS. 1G-1J are in that by adding an additional PE element 140 e.g., on the proximal and distal sides of the cooling channel 120 enables to measure the alignment of the PE element 140-2 with respect to the tissue.

In cases in which a PE emitting surface is at an angle with respect to the tissue (i.e., not parallel), the acoustic foot print on the tissue will be larger (like a shadow of a flashlight aimed at an angle onto a surface). The implication of a larger acoustic footprint is that the energy per area distributed on the tissue is smaller. Therefore, it is more difficult to ablate the tissue at the same energy level. If the angle of the emitting surface with respect to the tissue target surface is known, the required increase in the energy level can be calculated.

Hence, a potential advantage of a configuration having two or more inclined emitting surfaces is in that a system processor is in that it provides e.g., a system processor to measure the parallelism, the angles of the emitting surfaces with respect to the target tissue, compute the US beam energy required to ablate and adjust accordingly the PE element emitted US beam. In some embodiments, for example, an angle of the emitting surface 142 with respect to the target tissue 100 surface above 10 degrees, 15 degrees or 20 degrees requires an increase of 7%, 14% or 25% respectively.

A potential advantage in having an emitting surface positioned at an angle with respect to a second leveled emitting surface is in that such a configuration improves the detection of a signal emitted from the angled emitting surface and reflected from the tissue towards leveled emitting surface.

In some embodiments, the angled emitting surface is angled such that a first axis perpendicular to the angled emitting surface crosses a second axis perpendicular to the leveled emitting surface at a distance between 5 mm and 25 mm, 7 and 20 mm or 10 mm and 17 mm.

In some embodiments, and as shown in FIGS. 1G, 1H, 1I, 1J and 1K, PE element 140-1 is configured to detect an US signal emitted from PE element 140-2 and reflected off targeted tissue 110. Optionally and alternatively, PE element 140-2 is configured to detect an US signal emitted from PE element 140-1 and reflected off targeted tissue 110.

In some embodiments, a first PE element e.g., 140-1 is positioned such that it faces an expected US signal emitted from a second PE element e.g., 140-2 and reflected off targeted tissue 110.

Figures 1J, 1K:
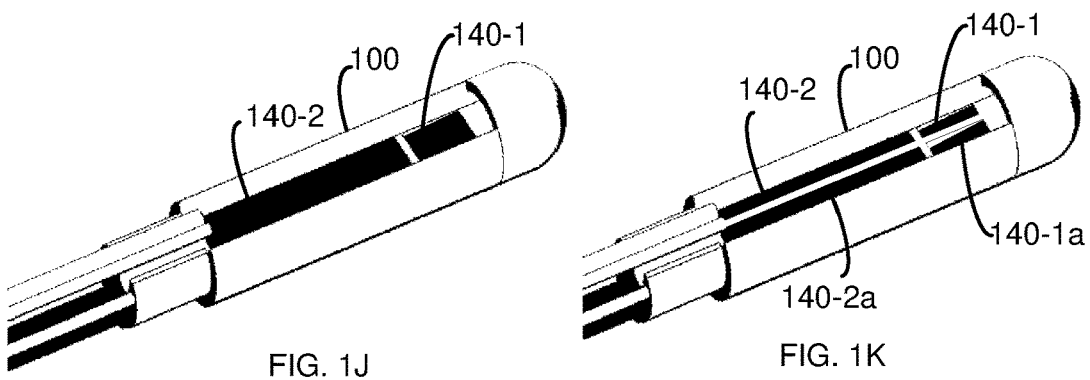

In the exemplary embodiments depicted in FIG. 1K, US transducer container 100 comprises two pair of PE elements 140-1/140-2 and 140-1a/140-2a placed side-by-side. A potential advantage ion this configuration is in that PE elements 140-1/140-2 and 140-1a/140-2a can be positioned and angled to provide imaging and ablative results suitable for any desired specific procedure.

In some embodiments, US transducer container 100 comprises a plurality of PE elements arranged axially along US transducer container 100. In some embodiments, two or more consecutive PE elements of the plurality of PE elements comprise at least two ablative PE elements. In some embodiments, the two or more consecutive PE elements define between them a gap (e.g., 528, FIGS. 5G, 5H, 5I) greater than 1 mm in width. In some embodiments, a first PE element comprises both an ablative and a sensor (imaging) configured to send and receive an US signal during ablation. In some embodiments, the ablative and a sensor (imaging) PE element is configured to detect signals returning directly to the PE element along an ablative US emission line.

In some embodiments, a second PE element acts only as sensor (imaging) that only receives signals between ablation pulses. A potential advantage in a second PE element acts only as sensor (imaging) is in that the treatment area is larger and there is an increased ability to detect returning signals that are deflected away from the direct ablation line. Additionally, a second PE element acts only as sensor (imaging) can detect signals from a close distance because the PE element it is at a resting state before the signal arrives and therefore, the arrived signal is cleaner (has less noise/ringing that are typically associated with an element that vibrate when it receives a signal).

In some embodiments, different PE elements of US transducer container 100 operate at different frequencies. E.g., ablative PE element/s operate in a frequency range greater than 8 mHz, while an imaging PE element/s operates at a different, lower range and works in pulse-echo mode. In this configuration, the ablative PE element ablates tissue and the imaging PE element transmits and receives its own imaging signal from the ablated area (pulse-echo mode). The pulse-echo mode configuration stems from the imaging PE element operates on lower frequencies and hence cannot detect the higher frequency signal of the ablative PE element. A potential advantage in this configuration is in that lower frequency PE elements allow for deeper signal penetration. Low frequency PE elements cannot be used for ablation purposes because of the greater difficulty in forming ablative lesions with low frequency US signals.

In some embodiments, PE elements used for imaging comprise an array of at least four smaller PE elements. A potential advantage in this configuration is in increased image resolution.

In some embodiments, a method for use of a combination of a scanning PE element and an ablating PE element or a single scanning and ablating PE element e.g., in ablating one or more ostia of the pulmonary veins and as depicted in FIGS. 1F to 1K, comprises:

Positioning US transducer container 100 at an ostium of a blood vessel;

rotating the transducer about its axis and scanning the vein ostium;

recording one or more returned signal/s from the tissue for creating a baseline image of the vein ostium;

concurrently or consecutively, measuring the vessel wall thickness;

ablating vessel tissue in the vein ostium in consecutive segments by rotating the transducer segmentally until full rotation is completed;

recording the returned signal/s of the ablated segments in real-time and creating a real-time image based on the one or more returned signals;

comparing the returned signal/s and/or images acquired during-ablation to the acquired baseline return signal/s and/or image created therefrom;

identifying changes in the return signal/s and/or image acquired during —ablation that represent changes in the tissue that correspond to ablation lesion formation; and terminating ablation after returned signal/s and/or image changes between baseline returned signal/s and/or image and acquired returned signal/s and/or image indicate an achieved predetermined level of ablation.

Catheter Ultrasound Transducer Cooling System

In some embodiments, and as shown in FIG. 1 catheter US transducer container 100 comprises a cooling system 200 configured to cool PE element 140 and maintain a container blood-contact surface 116 temperature at or below 45 degrees Celsius. In some embodiments, cooling system 200 comprises a cooling fluid inlet 152, a cooling fluid outlet 154 and a trough-form cooling channel 120 in between. In some embodiments, trough-form cooling channel 120 is defined by a floor 108, bordered by a first and a second side walls 122/124 extending from both sides of floor 108 and along both lateral sides of emitting surface 142. First and a second side walls 122/124 span between floor 108 and cover 130 and sealingly meet edges of container blood-contact surface 116 to form an aperture 118 in container 100.

In some embodiments, cover 130 comprises at least two surfaces: a PE element 140-facing surface and a blood contact surface 116 facing away from PE element 140. In some embodiments, blood-contact surface 116 is the outermost surface of cooling channel 120. In some embodiments, blood-contact surface 116 comprises an interface between cooling channel 120 and blood surrounding container 100 and catheter 106. In some embodiments, cover 130 forms a barrier that maintains the coolant fluid within cooling channel 120 and prevents blood from making contact with PE element 140 and/or cooling system 200. Such contact may lead to blood clotting.

In some embodiments, and as explained in greater detail elsewhere herein, walls 122/124 are inclined imparting a trapezoid cross-section to cooling channel 120 the smaller trapeze base forming floor 108. In some embodiments, the cross section of the cooling channel 120 has trapezoid geometry at least over 50% of its length. In some embodiments, the cross section of the cooling channel 120 has trapezoid geometry at least over 75% of its length.

Any one of PE elements 140/140-1/140-2/140-3 can function as an US ablating element and/or an US imaging transducer. For example, in FIG. 1G, PE element 140-2 may function as an US transducer whereas PE elements 140-1 and 140-3 may function as US ablation elements. Optionally and alternatively, and as described in detail elsewhere herein, in the embodiments depicted in FIGS. 1A-1G as well as embodiments described elsewhere herein PE element 140 may function as an US ablation element and/or an US transducer element. In some embodiments, and as discussed elsewhere herein, PE element 140 is disposed inside cooling channel 120 and is mounted on one or more posts 102. In some embodiments, dimensions of cooling channel 120 are equal to or larger dimensions of PE element 140. E.g., In some embodiments, a length of cooling channel 120 is at least the same as the length of PE element 140. In some embodiments, it is shorter than PE element 140.

Figure 2A:
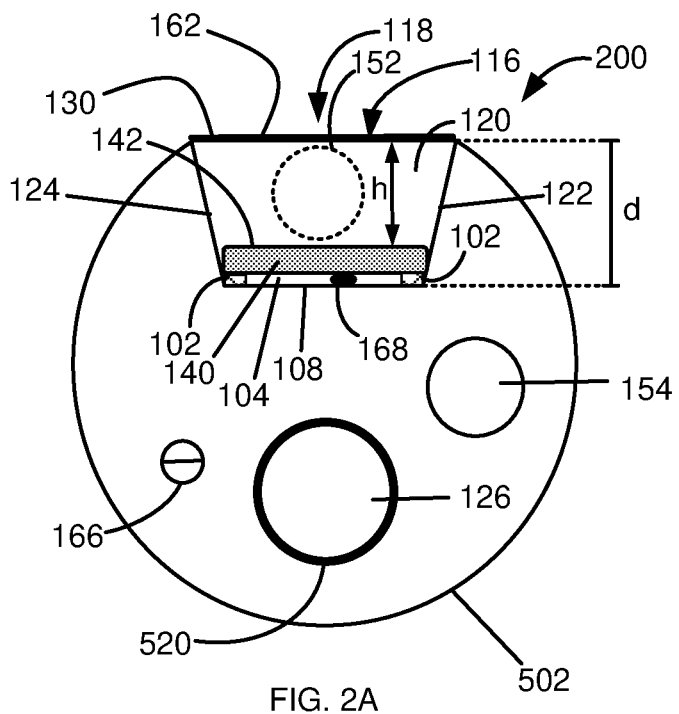
FIGS. 2A, 2B and 2C are cross section view simplified illustrations of the US transducer container cooling system in accordance with some embodiments of the current invention.
Figure 2B:
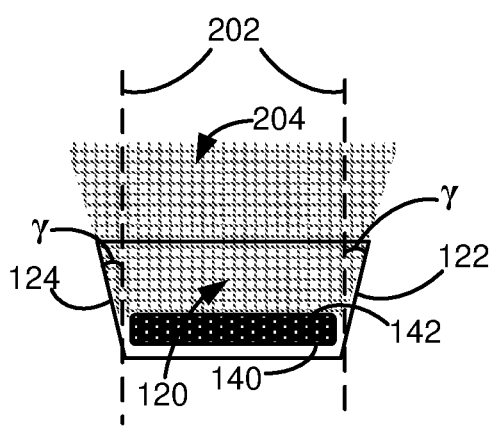
Figure 2C:
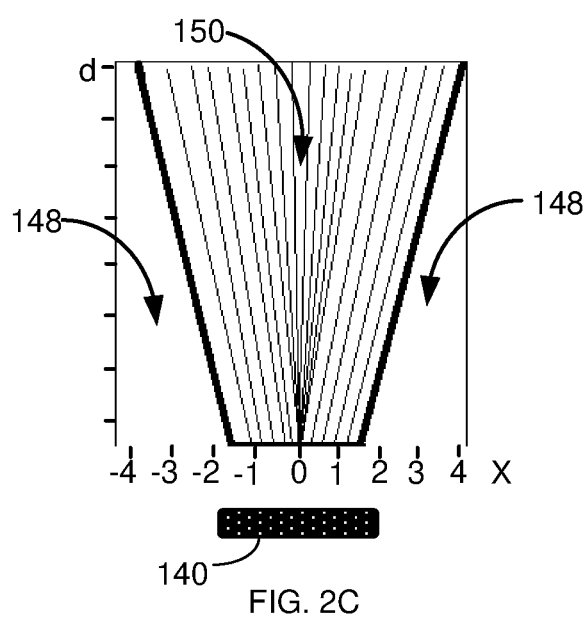

In some embodiments, and as shown in FIGS. 2A, 2B and 2C, walls 122/124 are inclined sloping radially inwards at an angle (y) between 1 and 45 degrees from the perpendicular 202 to floor 108. In some embodiments, angle (y) is between 10 and 30 degrees or 15 and 25 degrees from the perpendicular to floor 108.

A potential advantage in a trapezoid cross-section of cooling channel 120 is in that inclined walls 122/124 form an unobstructed pathway for an US beam 204 emitted from emitting surface 142 of PE element 140. A potential advantage in a trapezoid cross-section of cooling channel 120 is in that inclined walls 122/124 provide easy access to floor 108 for mounting of PE element 140 during manufacturing.

Catheter US Transducer Container

FIG. 2C, which is a thermal image of an US beam distribution pattern of an acoustic beam emitted from an US PE element 140 in perpendicular to the emitting surface 142 via cooling channel 120, depicts the pressure (Pmax) of the emitted beam along an X-axis (i.e., along a transverse cross-section of PE emitting surface 142) as a function of a height (h) (FIG. 2A) between emitting surface 142 and cooling channel 120 cover 130. As depicted in the exemplary embodiment shown in FIG. 2C, a margin clear of any US acoustic pressure is represented by a deep blue color 148 on both sides of an emitted beam 150 showing the full beam 150 span to be emitted with no interference. As shown in FIG. 2C, the acoustic beam emitted from an US PE element 140 is unobstructed as it travels through and out of cooling channel 120.

Figure 3A:
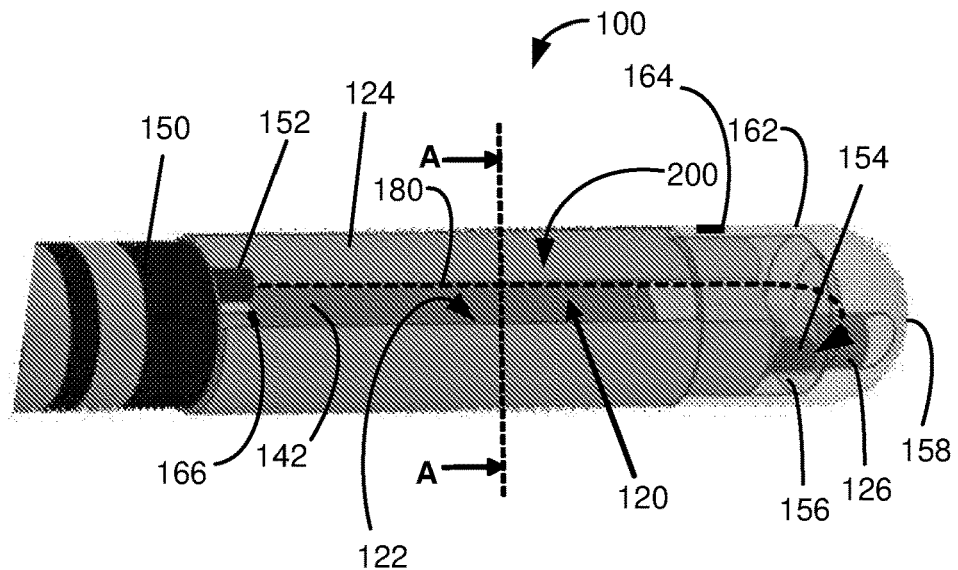
FIG. 3A is a perspective view simplified illustration of US transducer container cooling system and FIGS. 3B and 3C are graphs demonstrating heat distribution within the cooling system in accordance with some embodiments of the invention.
Figure 3B:
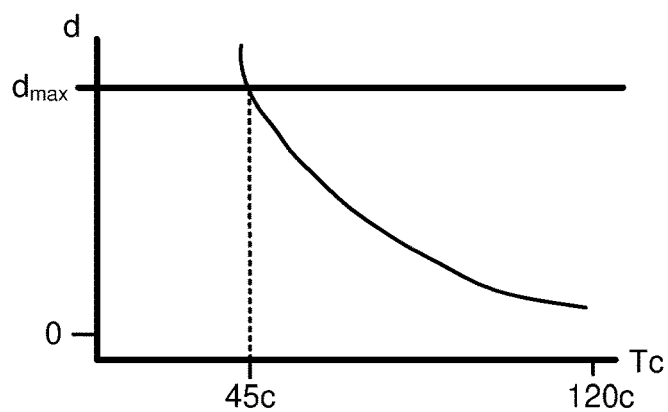
Figure 3C:
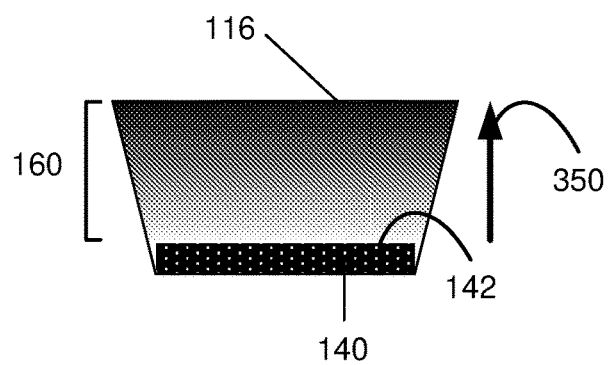

Reference is now made to FIG. 3A, which is a perspective view simplified illustration of catheter US transducer container 100 and US transducer container 100 cooling system 200 and to FIGS. 3B and 3C, which are graphs demonstrating heat distribution within cooling system 200 in accordance with some embodiments of the invention. In some embodiments, cooling system 200 is configured to cool PE element 140 as well as form a closed-circuit system, heat transfer buffer zone 160 between PE element 140 and blood-contact surface 116 configured to maintain a container 100 blood-contact surface 116 temperature at or below 45 degrees Celsius to decrease the risk of blood clotting and emboli generation. As shown in FIG. 3C, the temperature of the cooling fluid in buffer zone 160 drops as the distance of the fluid from PE element 140 increases as indicated by an arrow 350.

In some embodiments, buffer zone 160 is formed inside cooling channel 120 between emitting surface 142 and cover 130 by generating a temperature gradient in cooling fluid within cooling channel 120 as explained in greater detail elsewhere herein. In some embodiments, the cooling gradient is achieved by a laminar-uniform flow of the cooling fluid at least over emitting surface 142 of PE element 140 and formed by cooling channel 120 generally flat floor, flat emitting surface 142 of PE element 140 and flat cover 130, supplied by an acoustically matched dedicated cooling fluid inlet 152 at one end of channel 120 and evacuated by a dedicated cooling fluid outlet 154 at the other, opposite end of channel 120. In some embodiments, the rate of flow of the coolant fluid is adjusted to the viscosity of the fluid and fluid velocity is maintained below a threshold at which it becomes turbulent.

In some embodiments, a temperature sensor 166 at the blood-contact surface 116-blood interface (or temperature within the flow channel) controls the rate of flow rate needed to maintain a temperature of the blood barrier below a target temperature needed to prevent blood coagulation.

In some embodiments, the system is configured to vary the cooling fluid flow rate and change the effective temperature at the blood-contact surface 116-blood interface. For example, in some embodiments, the flow rate is increased to cool down the blood-contact surface 116-blood interface.

In some embodiments, the system is configured to vary the temperature of or at the fluid inlet 152 based on temperature readings of temperature sensor 166 at the blood-contact surface 116-blood interface (or temperature within the flow channel) and maintain an unchanged flow velocity.

Optionally, the system is configured to vary the temperature of or at the fluid inlet 152 and vary the flow of the cooling fluid based on temperature readings of temperature sensor 166 at the blood-contact surface 116-blood interface (or temperature within the flow channel).

The flow rate and variation in flow rate depends on at least one of the area cross-section of cooling channel 120, the area of blood-contact surface 116-blood interface, temperature of the cooling fluid and variation in vessel blood temperature. To cool down blood-contact surface 116-blood interface and given cooling channel 120 channel dimensions, the velocity of the cooling fluid over the ablating element in some embodiments, is between 5 cm/sec-60 cm/sec. In some embodiments, the velocity of flow is between 15 cm/sec-50 cm/sec. In some embodiments, the velocity of flow is between 20 cm/sec-30 cm/sec. is 25 cm/sec.

A potential advantage in this system configuration is in that the system cooling channel has a small cross-section e.g., smaller than a diameter of catheter 106 (between 0.01-0.5 of the diameter of catheter 106) configured to generate a velocity of flow sufficiently high to achieve efficient cooling, below 45 degrees Celsius at the blood-contact surface 116-blood interface.

The structure of cooling system 200 provides laminar-uniform flow over emitting surface 142 of PE element 140 in a direction indicated by arrow 180. In some embodiments, the flow rate of the cooling fluid is between 5 ml/sec and 400 ml/sec. In some embodiments, the flow rate of the cooling fluid is between 50 ml/sec and 300 ml/sec. In some embodiments, the flow rate of the cooling fluid is between 75 ml/sec and 200 ml/sec.

In some embodiments, container 100 comprises one or more temperature sensor 166 at the blood-contact surface 116 of container 100 cover 130 and the flow rate is adjusted in accordance with a temperature measured at blood contact surface 116. For example, when the measured temperature at blood-contact surface 116 exceeds 45 degrees Celsius, blood flow from inlet 152 is increased accordingly.

In some embodiments, container 100 comprises one or more temperature sensors 168 in gap 104 between PE element 140 and floor 108 of cooling channel 120 or adjacent to PE element 140. In some embodiments, the flow rate is adjusted in accordance with a temperature measured in gap 104 to monitor and control PE element 140 temperature during operation.

FIGS. 3B and 3C are a graph (FIG. 3B) and heat distribution map (FIG. 3C) depicting a temperature gradient in cooling channel 120 with respect to the level of the fluid layer measured by distance (L) from PE element 140 emitting surface 142. As shown in FIG. 3B, the greater the distance (L) between a fluid layer and PE element 140 emitting surface 142, the lower the temperature, dropping as shown in FIG. 3B from approximately 120 degrees Celsius at emitting surface 142 to approximately 45 degrees at blood-contact surface 116 which is at the greatest distance (dmax) from US beam emitting surface 142.

It is also noted in FIG. 3B, that the temperature continues to drop to below 45 degrees Celsius beyond blood-contact surface 116 in blood flow layers adjacent to blood contact surface 116. Optionally, the coolant fluid is cooled to below 37 deg C at blood contact surface 116, in which case the blood temperature which is normally at 37 deg C will not drop in the layers beyond the blood contact surface 116.

A potential advantage in the cross-section profile of cooling system 200 is in that the laminar flow of cooling fluid in cooling channel 120 generates an effective and uniform blood-contact surface 116-blood interface and provides for a rapidly formed homogeneous temperature profile of the blood-contact surface 116-blood interface with no heat zones.

A potential advantage in the cross-section profile of cooling system 200 is in that the laminar flow of cooling fluid in cooling channel 120 is configured to and effective in removal of gas (e.g., air) bubbles formed in cooling channel 120, e.g., bubbles adhered to PE element 140-facing surface of cover 130.

Component of the PE Element Cooling System

In some embodiments, a processor (not shown) is used to calculate and optimize signal transmission and sensing data (e.g., temperature, distance from organ wall, wall thickness, power application time, change in amplitude and phase of returned signal) to optimize power output (e.g., for ablation), transducer reliability and lesion size. In some embodiments, container 100 comprises a PE element temperature sensor 166 that communicates with the processor. The processor is configured to increase or decrease power input based on the data received from the piezoelectric temperature sensor.

In some embodiments, the system processor is configured to adjust the level of energy emitted from the PE element based on one or more of distance measured from the emitting surface of the PE element to said tissue wall, tissue thickness, duration of energy delivery, change in amplitude and/or phase of ultrasound signal returning from the tissue and reduction of recorded electrical potential signals.

In some embodiments, adjustment of the energy level is based on impedance measurement between one or more tissue contact electrodes 725 on positioner 702 and on one or more electrical electrodes, not in contact with the tissue located on the catheter 106 shaft or US transducer container 100.

In some embodiment, a processor (not shown) is configured to calculate speed of transducer rotation via a motor (not shown) positioned in the catheter handle (not shown) to optimize power output for optimal lesion creation based on sensing data (e.g., distance from organ wall, wall thickness, power application time, change in amplitude and phase of returned signal). Alternatively, and optionally, the processor is configured to calculate transducer rotation based on a gyroscope embedded within a handle (not shown) of catheter 106. A potential advantage of a gyroscope is in its ability to show absolute angles of the catheter/ultrasound transceiver that allows physicians to return to a registered angular position during the procedure.

In some embodiments, the processor receives data from both blood-contact surface temperature sensor 164 and PE element temperature sensor 166 and based on the current cooling fluid flow rate extrapolates a temperature gradient between emitting surface 142 and blood contact surface 116 and increases or decreases power input to PE element 140 accordingly.

In some embodiments, US transmission duty cycle is maintained greater than 60% to cool down US transducer PE element 140 without effecting the rate of energy transfer to tissue required to elevate tissue temperature above 50 deg needed to form tissue lesion.

Other means used to maintain a relatively cool temperature of PE element 140 comprise using a pulse repetition frequency to lower transducer temperature, increase flow rate, decrease coolant fluid temperature, lower duty cycle, and regulate voltage based on distance from tissue wall to regulate time needed for successful ablation.

Bubble Control

Bubbles commonly formed by cavitation effect or air trapped in the inlet and/or outlet tubes pose a common interference issue in US transmission by forming one or more non-acoustically matched surfaces that reflect portions of the emitted US beam in unexpected directions. This is especially found in configurations that involve cooling systems that circulate a coolant within a balloon enveloping the US transducer. Bubbles are often trapped and adhered to a curved wall of the balloon, where circulation is insufficient to dislodge the bubbles and when successful, the coolant fluid flow in the vicinity of the bubbles is turbulent and just arbitrarily moves the bubbles from one location to another.

Figure 4A:
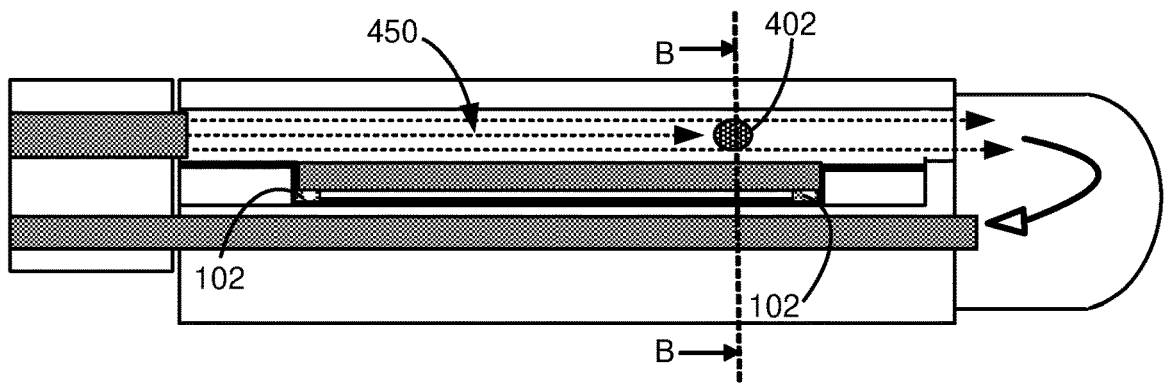
FIGS. 4A and 4B are longitudinal cross-section view and transverse cross section view simplified illustrations of the effect of laminar cooling fluid flow on bubbles in accordance with some embodiments of the current invention.
Figure 4B:
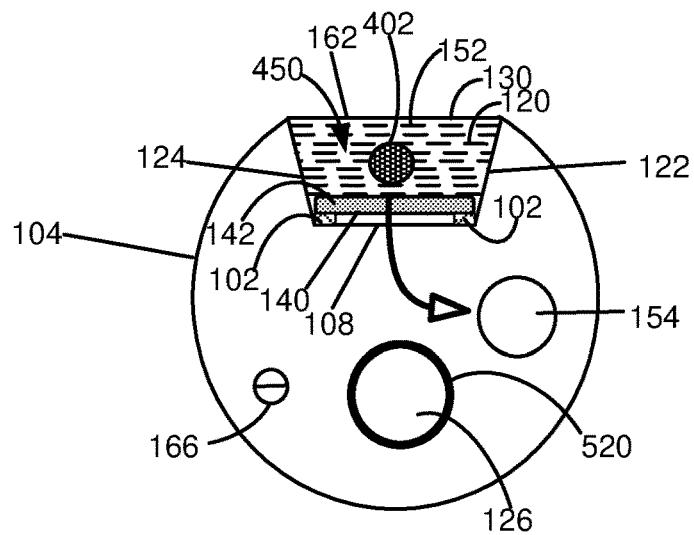

As shown in the exemplary embodiment depicted in FIGS. 4A and 4B, which are side cross-section view and transverse cross section view taken along line B-B, simplified illustrations of the effect of laminar cooling fluid flow on bubbles in accordance with some embodiments of the invention, a bubble 402, formed within cooling channel 120 is maintained away from emitting surface 142 and cooling channel cover 130 by laminar flow 450 and is carried towards cooling fluid outlet 154 positioned in cooling fluid diverting chamber 156 at tip 158 of the container 100 where it is suctioned out of the catheter 106 by vacuum within cooling fluid outlet 154 or by means of pressure head forcing the fluid towards the cooling fluid outlet 154.

In some embodiments, the confined channel cross-section adds to the effect of the laminar cooling fluid flow by limiting the wall surface to which a bubble may adhere as well as increase the fluid pressure applied to a bubble that appears. As shown in FIGS. 4A and 4B, bubbles that appear are urged into cooling fluid cooling fluid diverting chamber 156 at tip 158 of container 100 and by a down flow towards fluid outlet 154. An additional advantage in the configuration of the laminar flow in cooling channel 120 as well as the flow directionality is in that it removed risk of ultrasound transmission interreference due to air bubbles and negates the need for use of degassed fluid or in-line bubble detection sensors and/or traps.

In some embodiments, an area of a cross-section of cooling channel 120 constitutes between 0.01 and 0.5 of an area of a cross-section of the catheter 106 at the same location. In some embodiments, an area of a cross-section of cooling channel 120 constitutes between 0.1 and 0.4 of an area of a cross-section of the catheter 106 at the same location. In some embodiments, and at least one ultrasound transducer one or more PE elements 140 are disposed within and on a floor 108 of the channel 120.

A potential advantage of laminar cooling fluid flow within the cooling channel is in that heat transfer by the coolant is predictable and controlled by manually or automatically adjusting the flow rate and the flow parameters can be predefined (and simulated) with respect to the required ultrasound parameters.

A potential advantage of laminar cooling fluid flow within the cooling channel is in a uniform temp distribution throughout US transducer container 100 and faster flow adjustment expressed by faster control of blood contact surface temperature adjustment. Uniform temperature eliminates hot zones from forming at the blood contact surface 116.

In some embodiments, the maximal volume of the coolant within the US transducer container 100 is lower than 14,200 mm^3. In some embodiments, the maximal volume of the coolant within the US transducer container 100 is lower than 251 mm^3. In some embodiments, the volume of the coolant within the US transducer container 100 at any given time is between 1 mm^3 to 40 mm^3.

According to some embodiments, the US transducer is configured to be inserted into an organ (e.g., a blood vessel) via a catheter. In some embodiments, the external diameter of the US transducer container 100 is smaller than the diameter of a catheter 106 configured to insert the US transducer into an organ. In some embodiments, as shown in section A-A of FIG. 1, the cross section of container 100 is reduced at the level of cooling channel 120 cover 130. In some embodiments the cover 130 is made of a high heat absorbing material. In some embodiments the cover 130 is made of a low acoustic attenuation material. In some embodiments, cover 130 thickness is below 1 mm, below 0.5 mm or below 0.3 mm.

In some embodiments, the distance between the external surface of the US transducer and the tissue is monitored, such as the power supplied to the transducer is increased or decreased based on the monitored distance. In some embodiments, the distance between the transducer and the tissue is monitored, such as the power supplied to the transducer is increased or decreased based on the monitored distance. In some embodiments, the distance between the transducer and the tissue is monitored, such as the power supplied to the transducer is manually or automatically stopped if the monitored distance is below a predetermined safe distance. In some embodiments, a safe distance is defined by a distance above 1 mm. In some embodiments, a safe distance is defined by a distance above 2 mm. In some embodiments, a safe distance is defined by a distance above 5 mm. In some embodiments, the treatment duration and/or power is regulated based on analysis of the signals returned from tissue, detection of lesion formation in the tissue and completion of lesion created.

In some embodiments, the treatment duration and/or power is regulated based on one or more of the following measurements and calculations: distance from tissue, tissue thickness, transducer duty cycle, transducer pulse repetition frequency, voltage, amplitude of return signal from targeted area, rate of change of amplitude of returned signal, phase change of signal return from targeted area, reduction of recorded electrical potential signals e.g., signals recorded from the pulmonary veins and/or impedance measurement between a tissue contact electrode attached to the positioner 702 and a non-contact electrode attached to the catheter shaft or US housing. In some embodiments the US transducer comprises one or more computing units which receive sensors data as an input and outputs transducer operation parameters.

Transducer Design and Manufacture

Figure 5A:
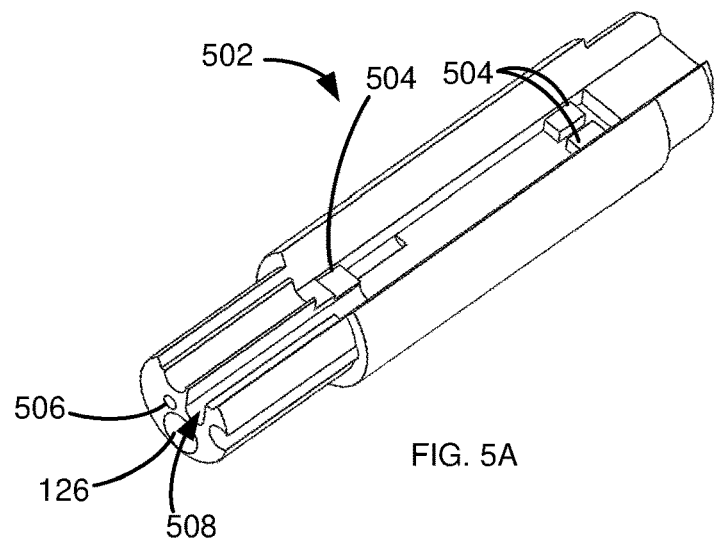

Reference is now made to FIGS. 5A, 5B, 5C, 5D, 5E, 5F, 5G, 5H and 5I, which are perspective view and cross section view simplified illustration of method of manufacturing a container transducer in accordance with some embodiments of the invention. As shown in FIG. 5A, a container 100 comprises a housing 502 comprises a trough-shaped fluid channel 120 having one or more supports 504 for PE element 140.

In some embodiments, PE element 140 support 504 are made of non-electrically conductive high temperature capacity material so that heat produced by PE element 140, positioned on supports 504, during operation is absorbed by the proximal and distal PE element 140 supports 504. In some embodiments, US PE element 140 comprises a middle partition made of a non-electrically conductive material that insulates between transducer electrodes connected at the distal end and the proximal end of the transducer ceramic.

In some embodiments of the current invention, the catheter US transducer comprises an internal heat conducting lumen, connected at its distal end to one or more of: US transducer surface, transducer support, thereby transferring heat out of the US transducer.

In some embodiments, housing 502 comprises an electrical conduit 506 for a PE element 140 temperature sensor 166 and a conduit 508 for electrical wiring as will be explained in greater detail herein. In the exemplary embodiment shown in FIG. 5B, an electrical wire 510 has been inserted into housing 502 and laid out prior to being connected to PE element 140.

FIGS. 5C and 5D, which are side cross-section view simplified illustrations of wiring options for PE element 140 in accordance with some embodiments of the invention. As shown in FIG. 5C, wiring of PE element 140 comprises two or more electrodes, a first electrode 512 along PE element 140 emitting surface 142 and a second electrode 514 along an opposite surface of PE element 140 facing floor 108 of cooling channel 120. Electrodes 512 and 514 are isolated from each other.

Alternatively, and optionally, and as shown in FIG. 5D, wiring of PE element 140 comprises two or more electrodes, a first electrode 516 along at least a portion of PE element 140 emitting surface 142 and around one end of PE element 140 and a second electrode 518 along at least a portion of an opposite surface of PE element 140 facing floor 108 of cooling channel 120 and around an opposite tip 158-facing end of PE element 140. Electrodes 516 and 518 are isolated from each other by one or more gaps 530/536 on the emitting surface 142 as well as on the opposite surface facing floor 108 respectively.

In some embodiments, one or more gaps 530/536 are bridged by an insulating adhesive. In FIG. 5D, the gap 536 on the emitting surface 142 of PE element 140 is bridged by an insulating adhesive 532.

A potential advantage of the wiring configurations is in that this configuration nullifies the need to isolate PE element 140 with non-conductive material, e.g., Parylene. This is achieved by positioning at least two contacts on generally opposite sides of the PE element 140, while maintaining and the PE element 140 circumferentially insulated with insulating material e.g., an electrical insulating adhesive. This prevents any potential electrical short between the two sides of the PE element.

A potential advantage in the use of a non-conductive material, e.g., Parylene to isolate PE element 140 is in that it simplifies the manufacturing process and is less expensive than other commonly used techniques. Reference is now made to FIG. 5E, which is a cross section of US transducer container 100 as taken along section C-C shown in FIG. 5B and shows wire 510 exiting conduit 508 and placed in contact with tip 158-facing end of PE element 140. In some embodiments, container cover 130 comprises one or more micro outlet ports 195 that allow fluid outflow from cooling channel 120 into the surrounding blood stream. A potential advantage of micro outlet ports is in that fluid exiting the micro ports washes off any blood residue/charring that may form during the ablation process.

FIG. 5F, is a cross section view simplified illustration of housing 502 electrical and fluid passages to catheter 106 as viewed from a direction indicated in FIG. 5B by an arrow 550. As shown in the exemplary embodiments depicted in FIG. 5F, housing 502 comprises conduits for cooling fluid inlet 152 tube and cooling fluid outlet 154 tube and a transducer housing support tube 520 having a lumen 126. In some embodiments, transducer housing support tube 520 and lumen 126 are sized to accommodate a guidewire 524 conducting tube 526 . . . In some embodiments, housing 502 comprises one or more conduits 508 for one or more ablation PE elements 140 coaxial cables and one or more conduits 522 for one or more inclined PE elements 140 coaxial cables.

Figure 5G:
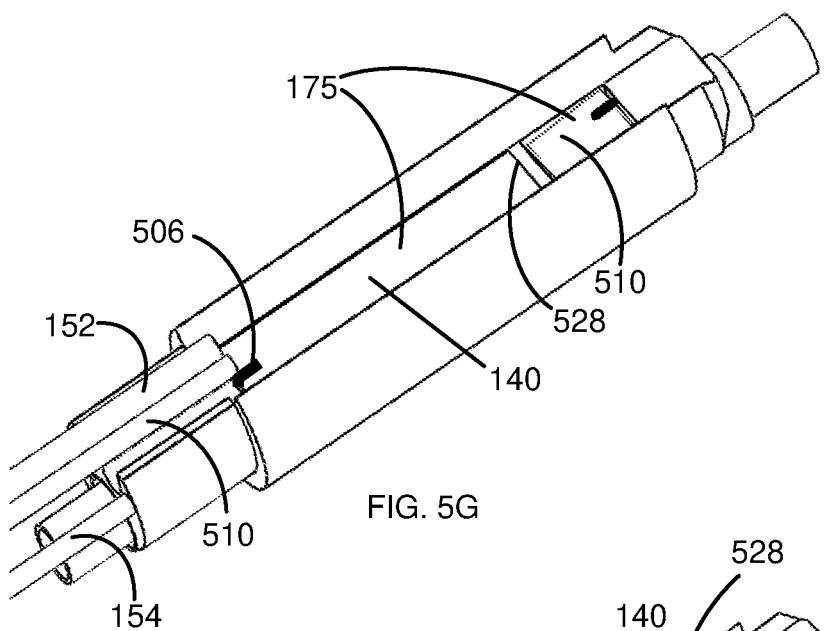
Figure 5H:
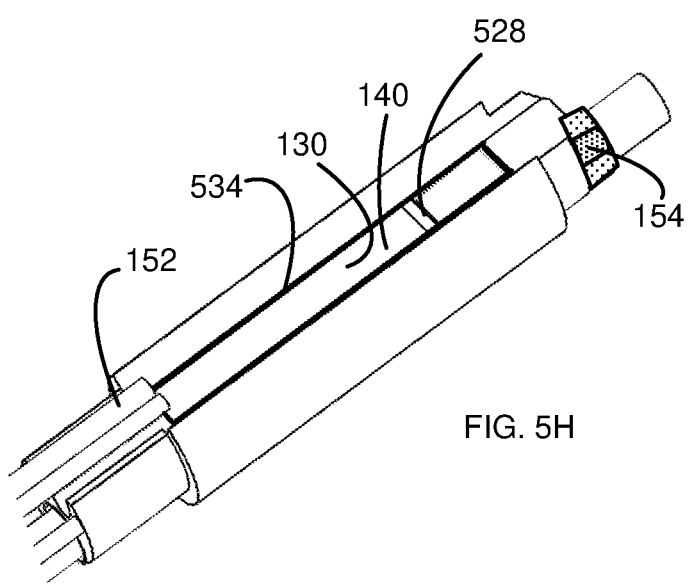
Figure 5I:
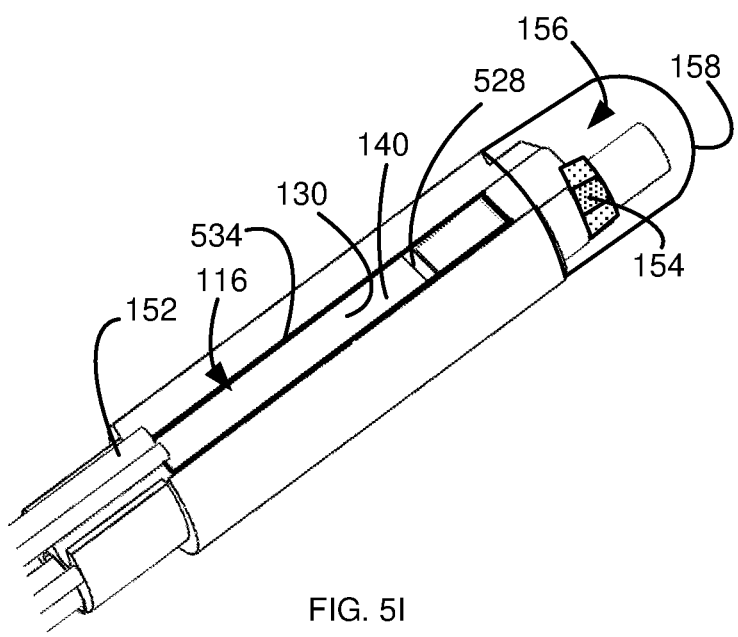

FIGS. 5G, 5H and 5I depict the manufacturing process of US transducer container 100 following the electrical wiring of US transducer container 100. FIG. 5G shows the stage of manufacturing following the previous stages described herein and comprises connecting electrical conductors 506/510 to the corresponding ends of PE element 140 in accordance with the connection options described elsewhere herein. The step of connection of electrical wires is followed in some embodiments, and as shown in FIG. 5H by attaching fluid inlet 152 and fluid outlet 154 to a cooling fluid diverting chamber 156 within tip 158 of the container as shown in FIG. 5I. The perimeter 534 of PE element 140 is sealed to walls 122/124 of cooling channel 120 and posts 102 with a flexible isolating and fluid proofing adhesive e.g., Epoxy adhesive, UV adhesive or Silicon adhesive (e.g., Dymax 204-CTH, Dymax 1191, Epo-Tek 301 or Epo-Tek 353ND) thus Insulating cover 130 is comprises a polymer (e.g., Polyester or Pebax®) is then placed over housing 502 as in shrunken (e.g., by exposure to heat) to tightly seal housing 502.

The process is finalized by attaching cooling channel cover 130 over housing 502 and non-spherical part of the container tip 156.

Figure 6:
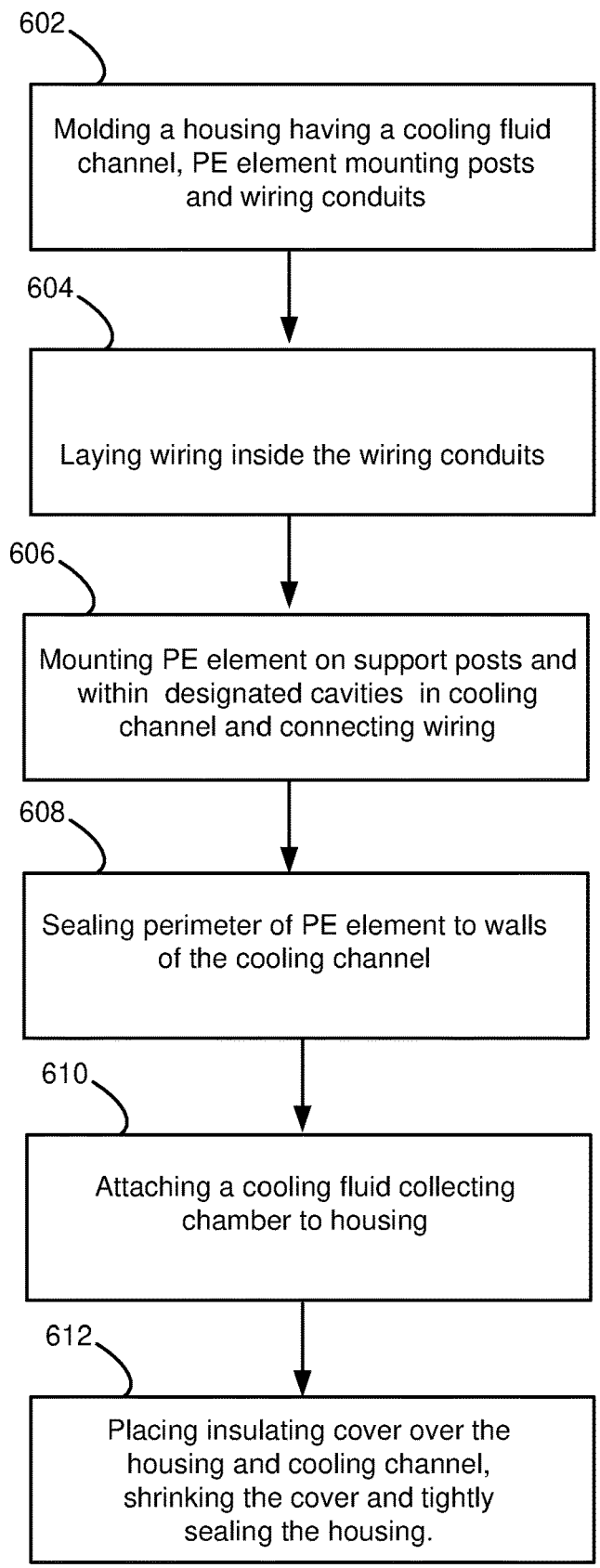
FIG. 6 is a flow chart of a method of manufacture and assembly of an US transducer container in accordance with some embodiments of the invention.

Reference is now made to FIG. 6, which is a flow chart of a method of manufacture and assembly of a US transducer container 100 in accordance with some embodiments of the invention. As shown in FIG. 6, the method comprises at 602 molding a housing 502 comprising one or more fluid conduits 152/154, one or more electrical conduits 506/510, one or more temperature sensor 166 conduits, one or more main catheter lumen 126, and one or more trough-shaped cooling channels 120.

In some embodiments, cooling channel 120 comprises a trough-form cooling channel 120 defined by a floor 108 including one or more posts 102 and bordered by a first and a second side walls 122/124 extending from both sides of floor 108 and along both lateral sides of emitting surface 142 and meet edges of container blood-contact surface 116 to form an aperture 118 in container blood-contact surface 116.

At 604, electrical conduit 506/510 of PE element 140 is laid within the respective conduits, in communication with and leading through catheter 106 to a respective source/s of power and/or communication (not shown).

At 606, PE element 140 is mounted on one or more posts 102 and connected to electrical conductors 506/510 as explained in detail elsewhere herein. In some embodiments, and optionally, the method comprises coating PE element 140 with a dielectric layer. In some embodiments, and optionally, the method comprises applying a dielectric material between ends of electrical conductors 506/510 connected to PE element 140. At 608, sealing the perimeter of PE element 140 to walls 122/124 of cooling channel 120 with a flexible isolating and fluid proofing adhesive and at 610 attaching a cooling fluid diverting chamber 156 and tip 158 of the container. In some embodiments, steps 606 and 608 are combined to a single step. The process is completed by placing over housing 502 an insulating covers a portion of which, in some embodiments, comprises cover 130, shrinking the cover (e.g., by exposure to heat) and tightly sealing housing 502 and cooling channel 120.

Positioner

Figure 7A:
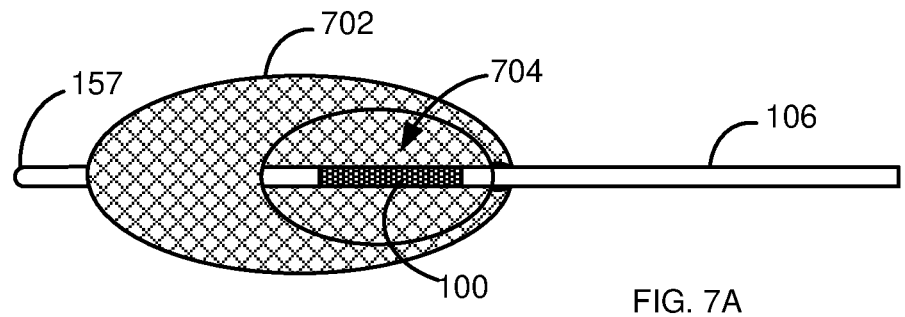
FIGS. 7A, 7B, 7C, 7D, 7E, 7F, 7G and 7H are plan view and perspective view simplified illustrations of a positioner 702 for an US transducer container in accordance with some embodiments of the invention.
Figure 7B:
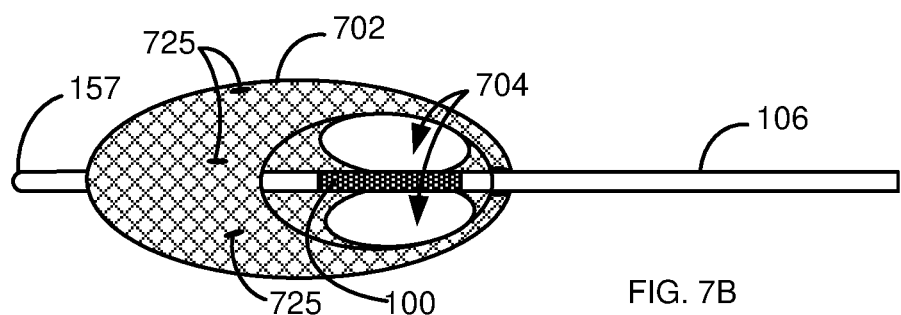
Figure 7C:
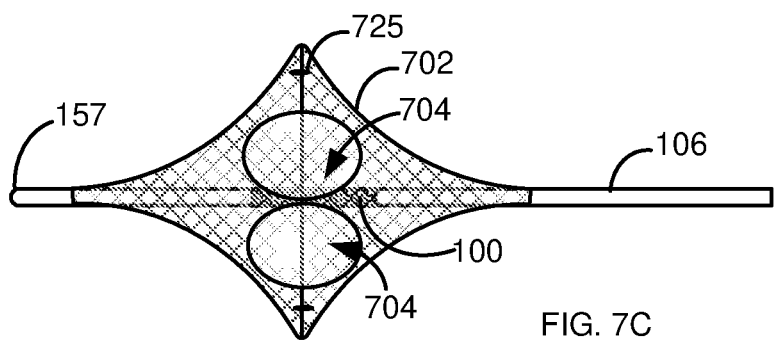

Reference is now made to FIGS. 7A, 7B, 7C and 7D which are plan view and perspective view simplified illustrations of a positioner 702 for a catheter 106 carrying a US transducer container 100 as disclosed herein. In some embodiments, catheter 106 comprises an expandable positioner 702 enveloping at least a portion of US transducer container 100. In some embodiments, positioner 702 is mounted on a catheter inserted through catheter 106. In some embodiments, positioner 702 is an integral part of catheter 106. In some embodiments, and as shown in FIGS. 7A, 7B and 7C, positioner 702 envelops US transducer container 100. In some embodiments, positioner 100 comprises one or more openings 704, the diameter of which is greater than the diameter of the US beam emitted through the opening 704 so that positioner 702 does not interfere with propagation of the beam. In some embodiments, positioner 702 is made of a shape memory resilient biocompatible material, e.g., Nitinol. In some embodiments, positioner 702 is a non-occluding positioner configured to allow blood flow therethrough.

In some embodiments, positioner 702 comprises a cage-like geometry. In some embodiments, positioner 702 comprises a basket-like geometry. In some embodiments, positioner 702 comprises a cylinder-like geometry. In some embodiments, dimensions of a cylindrical positioner 702 are between 10 mm-30 mm in diameter and 7 mm-60 mm in length. In some embodiments, dimensions of a cylindrical positioner 702 are between 15 mm-25 mm in diameter and 10 mm-50 mm in length. In some embodiments, dimensions of a cylindrical positioner 702 are between 17 mm-20 mm in diameter and 8 mm-40 mm in length.

In some embodiments, the geometry of positioner 702 and location of openings 704 in positioner 702 is non-uniform e.g., the openings 704 are located at the distal portion of positioner 702 such that one portion of positioner 702 e.g., a proximal portion, provides mechanical support and another portion e.g., a distal portion provides less mechanical support and more exposure (more openings 704) to allow for more effective acoustic ablation.

In some embodiments, positioner 702 comprises a detachable from the catheter. In some embodiments, positioner 702 comprises a detachable plug, e.g., configured to plug cavities in the left atrium such as Left Atrial Appendage following an ablation treatment.

In some embodiments, positioner 702 comprises contact and/or non-contact electrodes 725 and is configured to record electrical activity before, during and/or after ablation to monitor procedure effectiveness.

In some embodiments, and as depicted in FIGS. 7A and 7B, positioner 702 has an ovoid geometry. In some embodiments, and as depicted in FIG. 7C, positioner 702 comprises a positioner 702 has a diamond geometry or any other suitable geometry.

Figure 7D:
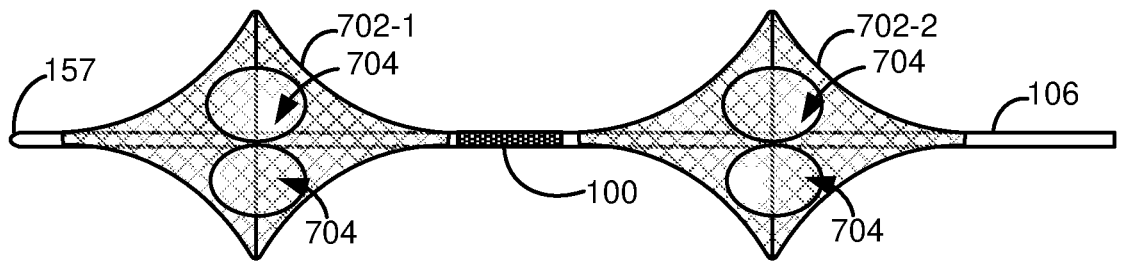
Figure 7E:
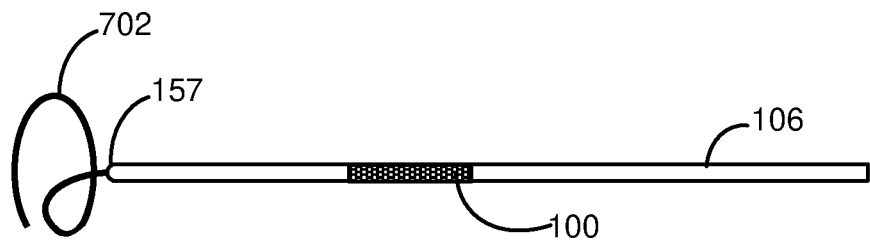
Figure 7F:
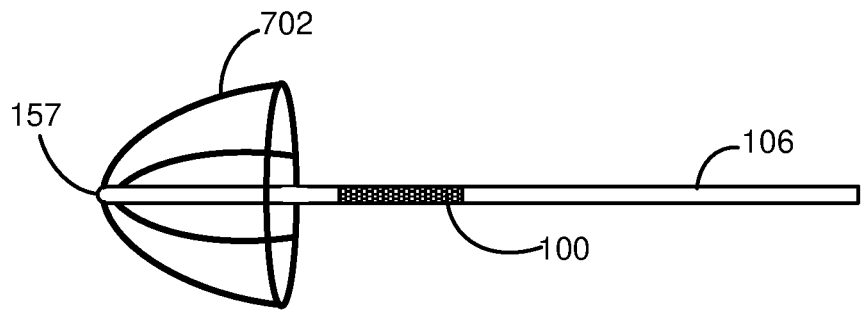
Figure 7G:
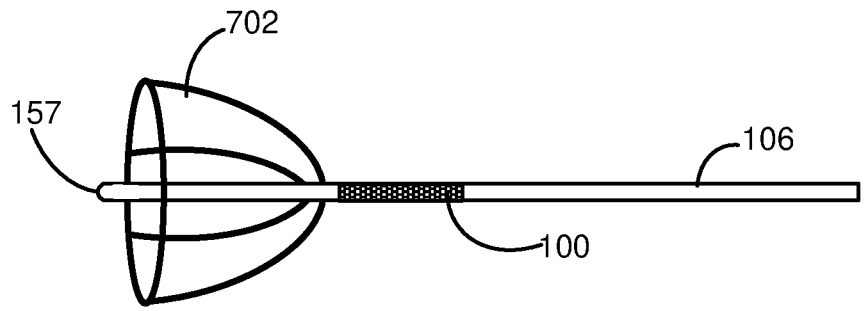
Figure 7H:
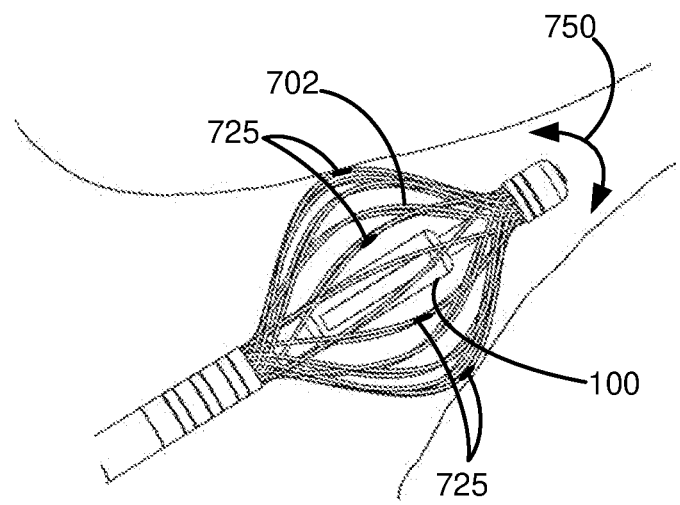

FIG. 7D, which is a perspective view simplified illustration of implementation of US transducer container 100 and positioner 702 in accordance with some embodiments of the invention. As shown in the exemplary embodiment depicted in FIG. 7D, US transducer container is implemented in contactless ablation of ostia of the pulmonary veins in the left atrium of the heart. In this procedure, a US transducer container 100 configuration can be employed using an ablative inclined PE element 140 and an imaging PE 140-1 as described elsewhere herein. Positioner 702 is expanded inside the left atrium lumen and directed towards one of the four main pulmonary veins ostia. Once the positioner 702 is positioned in contact with walls of the pulmonary vein ostium, US transducer container 100 is automatically positioned, generally centered in the ostium to allow safe ablation of the ostium margins. In some embodiments, US transducer container is configured to be rotatable within positioner 702 as indicated by arrow 750 and ablate a ring encompassing the margin of the pulmonary vein ostium. In some embodiments, US transducer container is configured to axially translate in a bidirectional manner within positioner 702 to better position US transducer container 100 within, for example, a pulmonary vein ostium. A potential advantage of this feature is in that linear movement of US transducer container 100 provides for linear ablation (e.g., in parallel to the axis of translation of US transducer container 100) of the tissue in selected anatomies.

In some cases, such as, for example atrial fibrillation treatment, the pulmonary vein is ablated to stop the ectopic cardiac action potential trigger. In such treatments, a balloon-type positioner or cooling balloon, commonly used in such procedures, is inflated to a point at which the balloon surface is urged against a vessel wall thus stabilizing the ablating element. However, when a cooling balloon is used to cool and center a transducer a blood vessel (e.g., within the pulmonary vein) and the balloon wall contacts the pulmonary vein tissue, blood might be trapped and pooled between the balloon and the tissue. The pooled blood may potentially coagulate due to heat generated by the tissue during ablation. Deflation of the balloon at the end of the procedure may release the newly formed blood clot which may become a stroke risk.

A potential advantage of a non-occluding positioner is in that it is configured to allow blood to flow therethrough significantly reducing or altogether preventing blood pooling and/or clotting and formation of blood embolism.

Jet Effect

Figure 8:
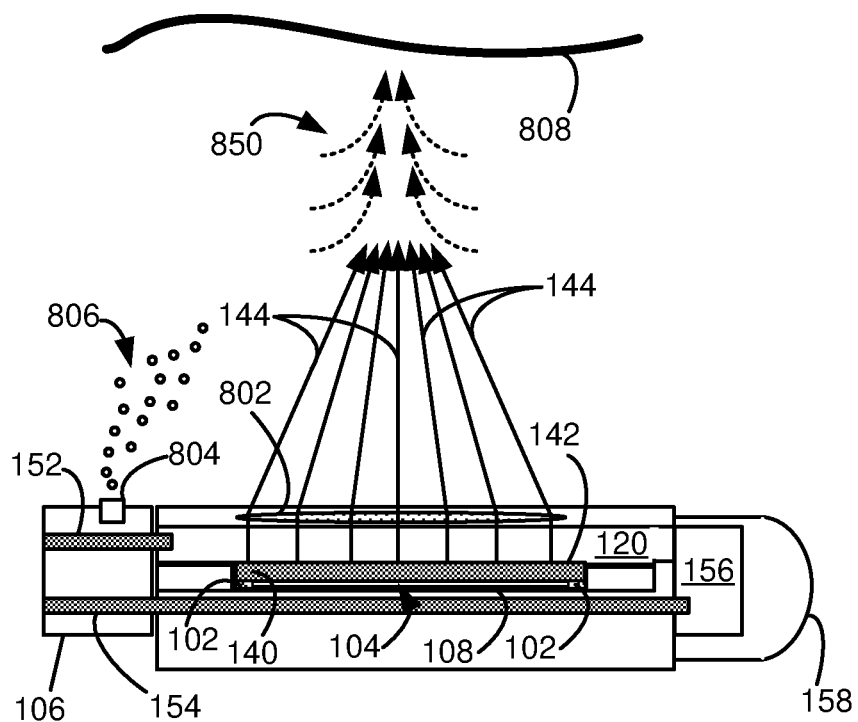
FIG. 8 is a cross section view simplified illustration of a jet effect generated by an US transducer container in accordance with some embodiments of the invention.

Reference is now made to FIG. 8, which is a cross-section view simplified illustration of implementation of a catheter US transducer container in accordance with some embodiments of the invention. In some embodiments, US transducer container 100 is sized and fitted to be positioned along or within a catheter 106. In some embodiments, US transducer container 100 comprises a collimating acoustic lens 802.

To the surprise of the authors of this disclosure it was observed that in some embodiments, collimated beam energy generated from a suitably designed US transducer PE element 140 generates a jet effect 850 in surrounding blood stream having the same temperature as that of the surrounding blood stream. In some embodiments, the collimated beam energy is above 50 W/cm^2. In some embodiments, the collimated beam energy is above 70 W/cm^2. In some embodiments, the collimated beam energy is above 90 W/cm^2.

A potential advantage in such a jet effect 850 is in that a jet aimed at a treatment area cools the tissue wall 808 at the point of penetration of the ultrasound beam into the tissue and prevents tissue charring.

In some embodiments, catheter 106 comprises one or more therapeutic agent delivery nozzles 804 configured to deliver a therapeutic agent 806 into the blood stream, e.g., up-stream to US transducer container 100 so that therapeutic agent 806 flows into emitted US beam 204 and is driven by the jet effect 850 towards the tissue 808.

It has also come to be known to the authors of this disclosure that too small a cross-section dimension (e.g., area) does not generate a jet effect or that the generated jet would not be effective in driving a therapeutic agent 806 towards a small tissue 808 area. Alternatively, a too large cross-section dimension (e.g., area) would require a high level of driving energy, beyond the maximal energy requirement for the device.

It was found that in some embodiments, an optimal cross-section dimension (e.g., area) for generating a jet effect sufficiently effective in driving a therapeutic agent 806 towards a small tissue 808 area should be sufficiently small (e.g., high energy per cross-section area) and is in the range between 8 mm^2 to 30 mm^2. In some embodiments, an optimal cross-section dimension (e.g., area) is in the range between 12 mm^2 to 20 mm^2. In some embodiments, an optimal cross-section dimension (e.g., area) is in the range between 14 mm^2 to 16 mm^2.

Figure 9:
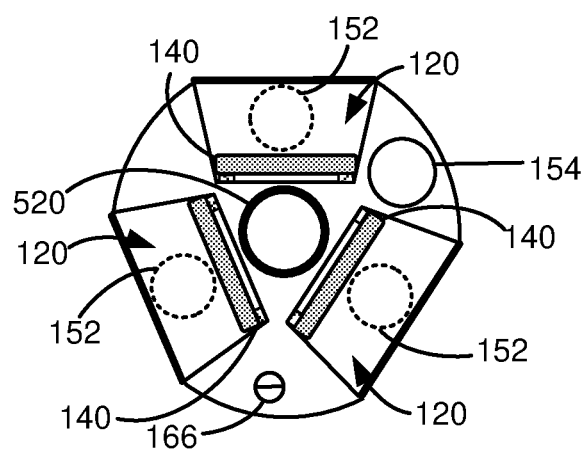
FIG. 9 is a transverse cross-section simplified illustration of a multidirectional US transducer container, according to some embodiments of the invention.

FIG. 9 is a transverse cross-section simplified illustration of a multidirectional US transducer container, according to some embodiments of the invention. In some embodiments, a multidirectional US scanner/ablating transducer container 900 includes a plurality of PE Elements 140, arranged circumferentially about a longitudinal axis of container 900. In some embodiments, each PE element is arranged within a cooling channel 120 and includes coolant fluid inlet and outlet and electrical conductors as explained elsewhere herein.

In some circumstances, in addition to catheter ablation for atrial fibrillation treatment as explained in detail elsewhere herein, there is a need to form lesions (e.g., lesion lines) in non-pulmonary vein ostium locations e.g., between the left inferior pulmonary vein to the mitral valve, between the left pulmonary veins to the right pulmonary veins along the posterior wall (LA roof line & LA floor lines) and/or in selected areas in the left atrium where ectopic cardiac action potential triggers are identified.

Figure 10A:
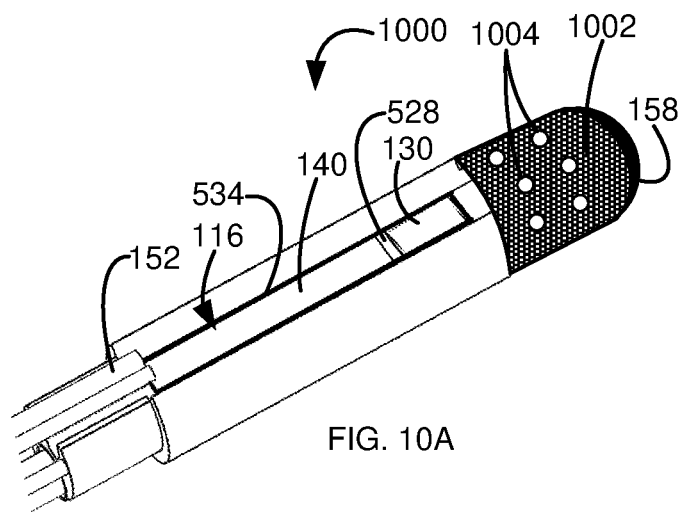
FIGS. 10A and 10B which are perspective view simplified illustrations of a combination US transducer/RF electrode catheter container, according to some embodiments of the invention.
Figure 10B:
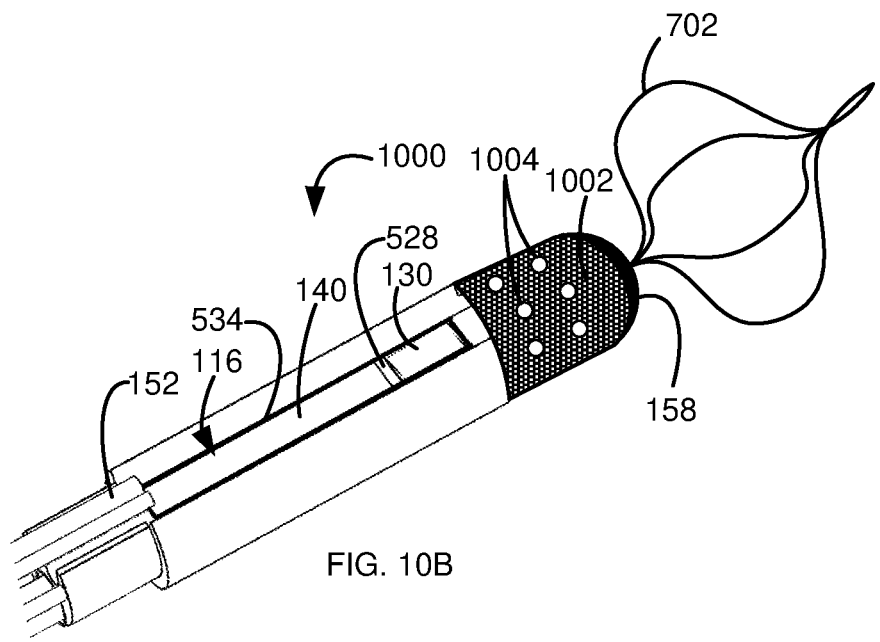

Reference is now made to FIGS. 10A and 10B, which are perspective view simplified illustrations of a catheter US transducer container including one or more RF electrode tips forming an US transducer/RF combination catheter container 1000. In some embodiments, and as shown in FIGS. 10A and 10B, the US transducer/RF container 1000 tip 158 comprises a metallic material such as, for example, iridium/platinum, platinum, copper or gold. In some embodiments, the US transducer/RF combination catheter container 1000 tip 158 comprises an RF electrode 1002 electrically connected via one or more electrical conductors, similar to electrical conductors 506/510, to an RF power source (not shown). In some embodiments, container tip 158 comprises one or more irrigation ports 1004 configured to eject cooling fluid (e.g., saline) to cool RF treated lesions and/or tissue surrounding the treated lesions. In some embodiments, US transducer/RF combination catheter container 1000 RF electrode 1002 is configured to come in contact with tissue and form lesions at the tissue.

A potential advantage in an US transducer/RF combination catheter container is in the ability of the device to treat not only pulmonary veins (PV) ostia but also to form additional lesion lines that might be required or desired after completion of pulmonary vein electrical isolation.

A potential advantage in a US transducer/RF combination catheter container is in that such a combination container is configured to effect:
 a. Radially outward directed US ablation, resulting in circumferential pulmonary vein (PV) electrical isolation; and
 b. Point-by-point RF ablation targeting non-PV ectopic cardiac action potential triggers.

A potential advantage in a US transducer/RF combination catheter container is in that such a combination container is configured for combining different types of energy (e.g., US and RF energies) to increase treatment diversity of the device:
 a. Radially outward directed US ablation, resulting in circumferential pulmonary vein (PV) electrical isolation; and
 b. Forward directed contact RF ablation for specific non-PV ectopic cardiac action potential triggers.

In some embodiments, and as shown in FIG. 10B, US transducer/RF combination catheter container comprises a positioner 702. In some embodiments, positioner 702 is detachable. A potential advantage in this configuration is in that positioner 702 is detachable and configured to plug a cavity e.g., the left atrial appendage.

In some embodiments, positioner 702 is collapsible. In some embodiments, positioner 702 in the collapsed configuration is configured to be drawn into catheter 106. A potential advantage in this configuration is in that a tissue location can be treated initially with an US transducer, being maintained in place by positioner 702 as explained in detail elsewhere herein, followed by removal of positioner 702 e.g., by collapse and retrieval into catheter 106, followed by contact RF treatment employing container tip 158 RF electrode 1002.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A catheter ultrasound (US) transducer container, the catheter US transducer comprising:
 a housing;
 at least one cooling channel, oriented longitudinally along a longitudinal axis of the housing;
 a sealing cooling channel cover;

one or more piezoelectric (PE) PE elements positioned on a floor of said cooling channel and having an emitting surface facing said cover; and wherein said cooling channel has a trapezoid cross section at any point along said PE element.

2. The catheter US transducer container according to claim 1, wherein an emitting surface of at least one PE element is oriented in parallel to said cooling channel cover.

3. The catheter US transducer container according to claim 1, wherein said housing further comprises at least one fluid inlet opening to a proximal end of the cooling channel and at least one fluid outlet located at a distal end of said cooling channel.

4. The catheter US transducer container according to claim 1, wherein said container further comprises a fluid diverting chamber coupled to a distal end of said cooling channel.

5. The catheter US transducer container according to claim 1, wherein said housing comprises at least one post coupled to said floor of said cooling channel and supports said PE element, forming a gap between said floor and said PE element.

6. The catheter US transducer container according to claim 1, wherein said at least one PE element is angled with respect to said floor of said cooling channel.

7. The catheter US transducer container according to claim 1, wherein said cooling channel cover and said emitting surface of said PE element are parallel.

8. The catheter US transducer container according to claim 1, wherein said cooling channel comprises a trough-form disposed longitudinally along a longitudinal axis of said container and configured to promote laminar fluid flow through said cooling channel.

9. The catheter US transducer container according to claim 8, wherein said trough-form is configured to promote a temperature gradient in said fluid flowing along a distance (L) between said emitting surface of said PE element and said fluid channel cover.

10. The catheter US transducer container according to claim 9, wherein said trough-form is configured to promote a temperature gradient in said fluid flowing along a distance (L) between said emitting surface of said PE element and said fluid channel cover and maintain a temperature at said cooling fluid channel cover at or below temperature of blood surrounding said container.

11. The catheter US transducer container according to claim 1, wherein said container comprises a plurality of PE elements angled with respect to one another.

12. The catheter US transducer container according to claim 1, wherein said container comprises a plurality of PE elements at least one of which is angled with respect to said cooling channel floor.

13. The catheter US transducer container according to claim 1, wherein at least one of said PE elements is an ablative PE element and at least one of said PE elements is an imaging PE element.

14. The catheter US transducer container according to claim 1, wherein a first of said at least one PE elements is both an ablative and an imaging PE element.

15. The catheter US transducer container according to claim 1, wherein a first of said at least one PE elements is both an ablative and an imaging PE element and a second PE element of said at least one PE elements is only an imaging PE element.

16. The catheter US transducer container according to claim 1, wherein a first PE elements of said at least one PE elements operates at a low frequency and a second of said at least one PE elements operates at a high frequency.

17. The catheter US transducer container according to claim 1, wherein a depth (d) of the cross-section of said cooling channel is smaller than the radius of said housing.

18. The catheter US transducer container according to claim 1, wherein said catheter comprises at least one positioner, and wherein the at least one positioner is in a form selected from the group consisting of: a basket, a coil, and an umbrella.

19. The catheter US transducer container according to claim 1, wherein said PE element is in communication with a processor, said processor being configured to adjust the level of energy emitted from said PE element based on at least one parameter selected from the group consisting of: distance measured from the emitting surface of the PE element to said tissue wall, tissue thickness, duration of energy delivery, change in amplitude of ultrasound signal returning from the tissue, change in and/or phase of ultrasound signal returning from the tissue, and reduction of recorded electrical potential signals.

20. The catheter US transducer container according to claim 19, wherein said processor is configured to adjust fluid flow velocity in said cooling channel based on said beam energy level.

* * * * *